United States Patent
Deshpande et al.

(10) Patent No.: US 9,447,132 B2
(45) Date of Patent: *Sep. 20, 2016

(54) HIGHLY ACTIVE NUCLEOSIDE DERIVATIVE FOR THE TREATMENT OF HCV

(71) Applicant: Achillion Pharmaceuticals, Inc., New Haven, CT (US)

(72) Inventors: Milind Deshpande, Madison, CT (US); Jason Allan Wiles, Madison, CT (US); Akihiro Hashimoto, Branford, CT (US); Avinash Phadke, Branford, CT (US)

(73) Assignee: Achillion Pharmaceuticals, Inc., New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/252,290

(22) Filed: Apr. 14, 2014

(65) Prior Publication Data

US 2014/0309189 A1   Oct. 16, 2014

Related U.S. Application Data

(60) Provisional application No. 61/811,464, filed on Apr. 12, 2013.

(51) Int. Cl.

| | | |
|---|---|---|
| *A61K 31/70* | (2006.01) | |
| *C07H 19/10* | (2006.01) | |
| *C07H 19/048* | (2006.01) | |
| *A01N 43/04* | (2006.01) | |
| *C07H 1/00* | (2006.01) | |
| *A61K 31/7072* | (2006.01) | |
| *A61K 45/06* | (2006.01) | |
| *C07F 9/24* | (2006.01) | |
| *C07H 19/067* | (2006.01) | |
| *C07F 9/58* | (2006.01) | |
| *C07B 59/00* | (2006.01) | |
| *A61K 31/4709* | (2006.01) | |

(52) U.S. Cl.
CPC .............. *C07H 1/00* (2013.01); *A61K 31/4709* (2013.01); *A61K 31/7072* (2013.01); *A61K 45/06* (2013.01); *C07B 59/005* (2013.01); *C07F 9/2429* (2013.01); *C07F 9/2458* (2013.01); *C07F 9/585* (2013.01); *C07H 19/067* (2013.01)

(58) Field of Classification Search
CPC ............... A61K 31/4709; A61K 31/7072; A61K 45/06; A61K 2300/00; C07B 59/005; C07F 9/2458; C07F 9/2429; C07F 9/585; C07H 1/00; C07H 19/067
See application file for complete search history.

(56) References Cited

U.S. PATENT DOCUMENTS

| | | |
|---|---|---|
| 3,480,613 A | 11/1969 | Walton et al. |
| 3,792,039 A | 2/1974 | Erickson et al. |
| 5,449,664 A | 9/1995 | Verheyden et al. |
| 5,656,745 A | 8/1997 | Bischofberger et al. |
| 5,798,340 A | 8/1998 | Bischofberger et al. |
| 6,054,576 A | 4/2000 | Bellon et al. |
| 6,127,535 A | 10/2000 | Beigelman et al. |
| 6,162,909 A | 12/2000 | Bellon et al. |
| 6,174,868 B1 | 1/2001 | Anderson et al. |
| 6,225,460 B1 | 5/2001 | Bischofberger et al. |
| 6,284,458 B1 | 9/2001 | Anderson et al. |
| 6,303,773 B1 | 10/2001 | Bellon et al. |
| 6,339,151 B1 | 1/2002 | Shepard et al. |
| 6,391,542 B1 | 5/2002 | Anderson et al. |
| 6,423,489 B1 | 7/2002 | Anderson et al. |
| 6,433,159 B1 | 8/2002 | Anderson |

(Continued)

FOREIGN PATENT DOCUMENTS

| | | |
|---|---|---|
| WO | 9507920 A1 | 3/1995 |
| WO | 0232920 A2 | 4/2002 |

(Continued)

OTHER PUBLICATIONS

US 8,697,641, 04/2014, Phadke et al. (withdrawn).

(Continued)

*Primary Examiner* — Lawrence E Crane
(74) *Attorney, Agent, or Firm* — Knowles IP Strategies, LLC

(57) ABSTRACT

A deuterated nucleoside analog of the formula

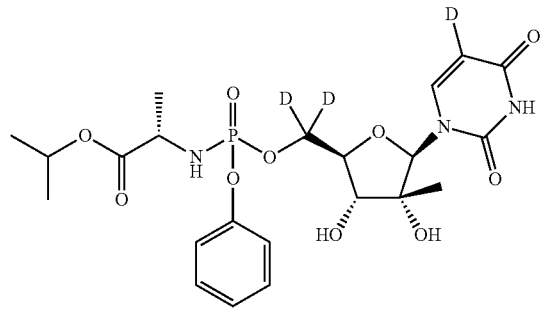

and the pharmaceutically acceptable salts thereof are provided by this disclosure. The disclosure also includes pharmaceutical compositions comprising a compound or salt of the formula and a carrier. Compounds and salts of this formula are useful for treating viral infections, including HCV infections. A method for treating a host afflicted with hepatitis C or other disorders is also presented that includes administering an effective treatment amount of a nucleoside or nucleotide that has deuterium with at least 50% enrichment at the 5'-position of the nucleoside or nucleotide.

13 Claims, 2 Drawing Sheets

(56) References Cited

U.S. PATENT DOCUMENTS

| | | |
|---|---|---|
| 6,482,932 B1 | 11/2002 | Beigelman et al. |
| 6,489,465 B2 | 12/2002 | Matulic-Adamic et al. |
| 6,503,890 B1 | 1/2003 | Uckun |
| 6,509,460 B1 | 1/2003 | Beigelman et al. |
| 6,528,640 B1 | 3/2003 | Beigelman et al. |
| 6,552,183 B1 | 4/2003 | Ramasamy et al. |
| 6,573,248 B2 | 6/2003 | Ramasamy et al. |
| 6,617,438 B1 | 9/2003 | Beigelman et al. |
| 6,642,206 B2 | 11/2003 | Ramasamy et al. |
| 6,673,918 B2 | 1/2004 | Bellon et al. |
| 6,777,395 B2 | 8/2004 | Bhat et al. |
| 6,797,815 B2 | 9/2004 | Matulic-Adamic et al. |
| 6,812,219 B2 | 11/2004 | LaColla et al. |
| 6,881,831 B2 | 4/2005 | Iyer et al. |
| 6,914,054 B2 | 7/2005 | Sommadossi et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,256,179 B2 | 8/2007 | Iyer et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,429,572 B2 | 9/2008 | Clark |
| 7,439,350 B2 | 10/2008 | Bischofberger et al. |
| 7,456,155 B2 | 11/2008 | Sommadossi et al. |
| 7,547,704 B2 | 6/2009 | LaColla et al. |
| 7,582,618 B2 | 9/2009 | Sommadossi et al. |
| 7,598,373 B2 | 10/2009 | Storer et al. |
| 7,601,703 B2 | 10/2009 | Shepard et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,625,875 B2 | 12/2009 | Gosselin et al. |
| 7,635,689 B2 | 12/2009 | LaColla et al. |
| 7,642,247 B2 | 1/2010 | Daifuku et al. |
| 7,662,798 B2 | 2/2010 | LaColla et al. |
| 7,772,197 B2 | 8/2010 | Daifuku et al. |
| 7,799,449 B2 | 9/2010 | Park et al. |
| 7,842,672 B2 | 11/2010 | Boojamra et al. |
| 7,879,815 B2 | 2/2011 | MacCoss et al. |
| 7,888,330 B2 | 2/2011 | Shields et al. |
| 7,902,202 B2 | 3/2011 | Sommadossi et al. |
| 7,906,619 B2 | 3/2011 | Phadke et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 8,071,567 B2 | 12/2011 | Devos et al. |
| 8,071,568 B2 | 12/2011 | Narjes et al. |
| 8,148,349 B2 | 4/2012 | Meppen et al. |
| 8,163,707 B2 | 4/2012 | Qiu et al. |
| 8,212,021 B2 | 7/2012 | Henschke et al. |
| 8,299,038 B2 | 10/2012 | Sommadossi et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,399,429 B2 | 3/2013 | Jonckers et al. |
| 8,415,321 B2 | 4/2013 | Schinazi et al. |
| 8,481,712 B2 | 7/2013 | Bhat et al. |
| 8,563,530 B2 | 10/2013 | Chang et al. |
| 8,575,119 B2 | 11/2013 | Wang et al. |
| 8,609,627 B2 | 12/2013 | Cho et al. |
| 8,614,180 B2 | 12/2013 | Phadke et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,686,045 B2 | 4/2014 | Longo et al. |
| 8,691,788 B2 | 4/2014 | Sommadossi et al. |
| 8,759,318 B2 | 6/2014 | Chamberlain et al. |
| 8,772,474 B2 | 7/2014 | Beigelman et al. |
| 8,841,275 B2 | 9/2014 | Du et al. |
| 8,859,756 B2 | 10/2014 | Ross et al. |
| 8,871,737 B2 * | 10/2014 | Smith et al. ........... C07H 19/06 514/47 |
| 8,877,731 B2 | 11/2014 | Beigelman et al. |
| 8,877,733 B2 | 11/2014 | Cho et al. |
| 9,090,642 B2 * | 7/2015 | Cho et al. ................. C07H 1/00 |
| 2003/0008841 A1 | 1/2003 | Devos et al. |
| 2004/0002476 A1 | 1/2004 | Stuyver et al. |
| 2004/0014957 A1 | 1/2004 | Eldrup et al. |
| 2004/0063658 A1 | 4/2004 | Roberts et al. |
| 2004/0072788 A1 | 4/2004 | Bhat et al. |
| 2004/0229839 A1 | 11/2004 | Babu et al. |
| 2005/0272676 A1 | 12/2005 | Bhat et al. |
| 2006/0205686 A1 | 9/2006 | Bhat et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0275912 A1 | 11/2007 | Bhat et al. |
| 2008/0207554 A1 | 8/2008 | Beigelman et al. |
| 2009/0176732 A1 | 7/2009 | Beigelman et al. |
| 2009/0181921 A1 | 7/2009 | Blatt et al. |
| 2009/0280084 A1 | 11/2009 | Schinazi et al. |
| 2009/0318380 A1 | 12/2009 | Sofia et al. |
| 2010/0003217 A1 | 1/2010 | Cretton-Scott et al. |
| 2010/0092460 A1 | 4/2010 | Blanchetot et al. |
| 2010/0151001 A1 | 6/2010 | Schott et al. |
| 2010/0152103 A1 | 6/2010 | Phadke et al. |
| 2010/0152128 A1 | 6/2010 | Attenni et al. |
| 2010/0216725 A1 | 8/2010 | Phadke et al. |
| 2010/0240604 A1 | 9/2010 | Beigelman et al. |
| 2010/0249068 A1 | 9/2010 | Beigelman et al. |
| 2010/0297079 A1 | 11/2010 | Almond et al. |
| 2010/0316594 A1 | 12/2010 | Sommadossi et al. |
| 2011/0245484 A1 | 10/2011 | Ross et al. |
| 2011/0251152 A1 | 10/2011 | Ross et al. |
| 2011/0306573 A1 | 12/2011 | Avolio et al. |
| 2012/0065156 A1 | 3/2012 | Jonckers et al. |
| 2012/0070411 A1 | 3/2012 | Beigelman et al. |
| 2012/0071434 A1 | 3/2012 | Smith et al. |
| 2012/0237480 A1 | 9/2012 | Or et al. |
| 2012/0251487 A1 | 10/2012 | Surleraux |
| 2012/0302538 A1 | 11/2012 | Wiles et al. |
| 2013/0017171 A1 | 1/2013 | Sommadossi et al. |
| 2013/0064793 A1 | 3/2013 | Surleraux et al. |
| 2013/0064794 A1 | 3/2013 | Surleraux et al. |
| 2013/0072528 A1 | 3/2013 | Bernstein et al. |
| 2013/0085133 A1 | 4/2013 | Severson et al. |
| 2013/0095064 A1 | 4/2013 | Surleraux et al. |
| 2013/0149283 A1 | 6/2013 | Sommadossi et al. |
| 2013/0172239 A1 | 7/2013 | Gao et al. |
| 2013/0172240 A1 | 7/2013 | Kapoor |
| 2013/0210757 A1 | 8/2013 | Huang et al. |
| 2013/0217644 A1 | 8/2013 | Mayes et al. |
| 2013/0217648 A1 | 8/2013 | Jonckers et al. |
| 2013/0225520 A1 | 8/2013 | Jonckers et al. |
| 2013/0237494 A1 | 9/2013 | Schott |
| 2013/0244966 A1 | 9/2013 | Milne et al. |
| 2013/0281686 A1 * | 10/2013 | Cho et al. ................. C07H 1/00 536/26.7 |
| 2014/0038916 A1 | 2/2014 | Wang et al. |
| 2014/0113958 A1 | 4/2014 | Hodges |
| 2014/0140955 A1 | 5/2014 | McGuigan et al. |
| 2014/0154211 A1 | 6/2014 | Girijavallabhan et al. |
| 2014/0206640 A1 | 7/2014 | Girijavallabhan et al. |
| 2014/0212382 A1 | 7/2014 | Schinazi et al. |

(56) References Cited

U.S. PATENT DOCUMENTS

| | | |
|---|---|---|
| 2014/0221304 A1 | 8/2014 | Verma et al. |
| 2014/0234253 A1 | 8/2014 | Walker et al. |
| 2014/0235567 A1 | 8/2014 | Verma et al. |

FOREIGN PATENT DOCUMENTS

| | | |
|---|---|---|
| WO | 03062257 A1 | 7/2003 |
| WO | 2004002999 A2 | 1/2004 |
| WO | 2004106356 A1 | 12/2004 |
| WO | 2006121820 A1 | 11/2006 |
| WO | 2007027248 A2 | 3/2007 |
| WO | 2008082601 A2 | 7/2008 |
| WO | 2009058800 A2 | 5/2009 |
| WO | 2010135569 A1 | 11/2010 |
| WO | 2012040127 A1 | 3/2012 |
| WO | 2012041965 A1 | 4/2012 |
| WO | 2012142523 A2 | 10/2012 |
| WO | 2013024155 A1 | 2/2013 |
| WO | 2013066991 A1 | 5/2013 |

OTHER PUBLICATIONS

Bartenschlager et al., "Replication of Subgenomic Hepatitis C Virus RNAs in a Hepatoma Cell Line", Science, vol. 285, (Jul. 1999), pp. 110-113.

Bartenschlager et al., "Viral and Cellular Determinants of Hepatitis C Virus RNA Replication in Cell Culture", Journal of Virology, 77(5), (Mar. 2003), pp. 3007-3019.

Chun et al., "Synthesis of Stable Isotope Labeled Analogs of the Anti-Hepatitis C Virus Nucleotide Prodrugs PSI-7977 and PSI-352938," Nucleosides, Nucleotides and Nucleic Acids, 30, (2011), pp. 886-896.

Corey et al., "One-Step Conversion of Primary Alcohols in the Carbohydrate Series to the Corresponding Carboxylic tert-Butyl Esters", Journal Organic Chemistry, 49, (1984), pp. 4735-4735.

Esaki et al., "Synthesis of Base-selectively Deuterium-labelled Nucleosides by the Pd/C-Catalyzed H—D Exchange Reaction in Deuterium Oxide", Heterocycles, The Japan Institute of Heterocyclic Chemistry, 66, (2005), pp. 361-369.

Gunic et al., "6-Hydrazinopurine 2'-Methyl Ribonucleosides and Their 5'-Monophosphate Prodrugs as Potent Hepatitis C Virus Inhibitors," Bioorganic & Medicinal Chemistry Letters, 17, (2007), pp. 2456-2458.

Gunic et al., "Cyclic monophosphate Prodrugs of Base-Modified 2'-C-Methyl Ribonucleosides as Potent Inhibitors of Hepatitis C Virus RNA Replication," Bioorganic and Medicinal Chemistry Letters, 17, (2007), pp. 2452-2455.

Harry-O'Kuru et al.,"A Short, Flexible Route toward 2'-C-Branched Ribonucleosides", Journal of Organic Chemistry, 62, (1997), pp. 1754-1759.

International Search Report for International Patent Application No. PCT/US2014/034021; International Filing Date: Apr. 4, 2014; Date of Mailing: Nov. 6, 2014; 6 Pages.

International Search Report of the International Searching Authority for International Patent Application No. PCT/US2014/034018; International Filing Date: Apr. 14, 2014; Date of Mailing: Jun. 27, 2014; 6 Pages.

Kang et al., "Synthesis and Characterization of Oligonucleotides Containing 5-Chlocytosine", Chem. Res. Toxicol. 17, (2004), pp. 1236-1244.

Leisvuori et al., "5',5'-Phosphodiesters and Esterase Labile Triesters of 2'-C-Methylribonucleosides," ARKIVOC, 8 (9), (2012), pp. 226-243.

Ozga et al., "Histidine Triad Nucleotide-binding Protein 1 (HINT-1) Phosphoramidase Transforms Nucleoside 5'-0Phosphorothioates to Nucleoside 5'—O-Phosphates*"' The Journal of Biological Chemistry, 285(52), (Dec. 24, 2010), pp. 40809-40818.

Pearson et al., "Characterization of Ectonucleotidases on Vascular Smooth-Muscle Cells" Biochem. J., 230, (1985), pp. 503-507.

Ross et al., "Synthesis of Diastereomerically Pure Nucleotide Phosphoramidates", The Journal of Organic Chemistry, 76, (2011), pp. 8311-8319.

Tolbert et al., "Preparation of Specifically Deuterated and 13 C-Labled RNA for NMR Studies Using Enzymatic Synthesis"; Journal of the American Chemical Society, 19(50), (Dec. 1, 1997), pp. 12110-12108.

Tolbert et al., "Preparation of Specifically Deuterated and 13C-Labeled RNA for NMR Studies Using Enzymatic Synthesis," Journal of American Chem. Soc., 119, (1997), pp. 12100-12108.

Written Opinion for International Patent Application No. PCT/US2014/034021; International Filing Date: Apr. 4, 2014; Date of Mailing: Nov. 6, 2014; 9 Pages.

Written Opinion of the International Searching Authority for International Patent Application no. PCT/US2014/034018; International Filing Date: Apr. 14, 2014; Date of Mailing: Jun. 27, 2014; 5 Pages.

* cited by examiner

HIGHLY ACTIVE NUCLEOSIDE DERIVATIVE FOR THE TREATMENT OF HCV

CROSS REFERENCE TO RELATED APPLICATION

This application claims the benefit of U.S. Provisional Application No. 61/811,464, filed Apr. 12, 2013, which is hereby incorporated by reference in its entirety.

SEQUENCE LISTING

The sequence listing 12033-034US1CorrectedSequenceListing.txt created on Nov. 24, 2015 is 698 bytes and is incorporated herein by reference.

BACKGROUND

An estimated 3% of the world's population is infected with the hepatitis C virus. The World Health Organization estimates that 150 million people are chronically infected worldwide. Of those exposed to HCV, 80% to 85% become chronically infected, at least 30% develop cirrhosis of the liver, and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus. HCV is classified as a member of the *Hepacivirus* genus of the family Flaviviridae. At least 4 strains of HCV, GT-1-GT-4, have been characterized. The HCV lifecycle includes entry into host cells; translation of the HCV genome, polyprotein processing, and replicase complex assembly; RNA replication; and virion assembly and release. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus.

There are several proteins in hepatitis C that have been targeted for drug therapy. NS5A is a zinc-binding proline rich hydrophilic phosphoprotein with no inherent enzymatic activity, which can be inhibited with certain non-nucleotide compounds. NS5B is a key enzyme which plays the major role in replicating HCV viral RNA using a viral positive RNA strand as a template, which has been inhibited with synthetic nucleoside derivatives. NS2-3 protease is an enzyme responsible for proteolytic cleavage between NS2 and NS3, which are non-structural proteins. NS3 protease is responsible for the cleavage of the non-structural protein downstream. RNA helicase uses ATP hydrolysis to unwind RNA.

Sofosbuvir (Sovaldi, see structure below) is a nucleoside phosphoramidate NS5B inhibitor approved in December 2013 for the treatment of HCV. The approved labeling recommends the following regimens: (i) for genotypes 2 and 3 a 400 mg once a day oral tablet in combination with ribavirin and (ii) for genotypes 1 and 4 a 400 mg once a day oral tablet (triple combination therapy) with ribavirin and pegylated interferon. The sofosbuvir treatment lasts 12 weeks for genotypes 1, 2 and 4 and 24 weeks for genotype 3. Sofosbuvir can also be used with ribavirin for the treatment of chronic hepatitis C patients with hepatocellular carcinoma awaiting liver transplantation for up to 48 weeks or until liver transplantation to prevent post-transplant HCV infection. The FDA granted Sovaldi Priority Review and Breakthrough Therapy designation based on data from several large clinical trials that indicated a sustained viral response (SVR) of twelve weeks in 50-90 percent of the trial participants. Patients who achieve "SVR12" are often considered cured.

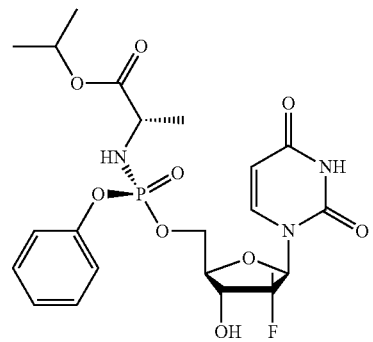

sofosbuvir

Alios BioPharma, Inc. licensed ALS-2200 to Vertex Pharmaceuticals Inc. for hepatitis C treatment development in June 2011. ALS-2200 is a mixture of diastereomers at a chiral phosphorus stereocenter. A single diastereomer, VX-135, is being developed by Vertex, and is currently in Phase II clinical trials. While the companies have not disclosed the chemical structure of VX-135, they have said that it is a uridine nucleotide analog prodrug, and an NS5B inhibitor. In 2013, the FDA placed VX-135 on partial clinical hold after three patients receiving high dosages of VX-135 showed liver toxicity. Lowering the dose of a nucleotide inhibitor to avoid toxicity can sometimes also compromise or lower efficacy. Vertex announced in January 2014 that VX-135 in combination with daclastavir (Bristol-Myers Squibb NS5A inhibitor) had completed a Phase 2a trial. In an intent-to-treat analysis, the sustained viral response rate four weeks after completion of treatment (SVR4) was 83% (10 of 12) in treatment-naïve genotype 1 infected individuals who received 200 mg VX-135 in combination with daclatasvir. One patient exhibited a serious adverse event of vomiting/nausea. The eleven remaining patients completed 12 weeks of treatment, for a completion of treatment rate (SVR4) of 91%.

Idenix Pharmaceuticals Inc. is developing IDX21437 for the treatment of hepatitis C, which is a uridine nucleotide prodrug NS5B inhibitor. The details of the chemical structure have not been released to date. In April 2014, Idenix announced that once-daily 300 mg IDX21437 for seven days led to a mean maximum reduction in viral load of 4.2-4.3 log 10 IU/mL in 18 treatment naïve patients with genotype 1, 2 or 3.

Despite progress in the area of hepatitis C treatment, there have also been a number of difficult setbacks. BMS-986094, a guanosine-based phosphoramidate for hepatitis C was pulled from clinical trials after the death of a patient due to heart failure in August 2012. BMS thereafter announced in 2013 that it was exiting the hepatitis C research area. Following the BMS drug withdrawal, Idenix Pharmaceuticals's similar NS5B inhibitor, IDX 19368, which shares the same active metabolite, BMS-986094, was placed on clinical hold and ultimately discontinued. This followed the previous clinical hold and discontinuation of development of the nucleotide prodrug IDX184 for the same indication.

It is known that effective treatment against hepatitis C includes combination therapy, due to the onset of viral resistance during monotherapy. Given the documented challenges of developing optimal hepatitis C agents, and the fact that multiple optimal agents are required for effective therapy, there is a strong need for additional hepatitis C agents.

SUMMARY

It has been surprisingly discovered that the 2'-methyl 5'-deuterated uridine phosphoramidate of Formula I, including Formula II, Formula IIA, Formula IIB, Formula IIIA, or Formula IIIB, or a pharmaceutically acceptable salt thereof, wherein deuterium has an enrichment over hydrogen of at least 90%, and wherein $R^1$ and $R^2$ are independently deuterium or hydrogen, is a superior NS5B inhibitor for the treatment of hepatitis C. In one embodiment, $R^1$ is deuterium and $R^2$ is hydrogen.

Formula I

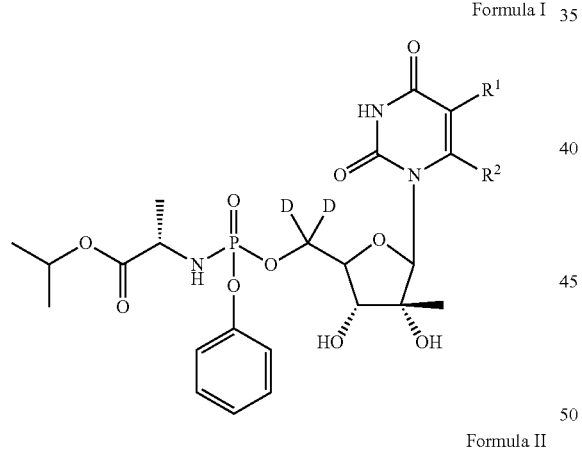

Formula II

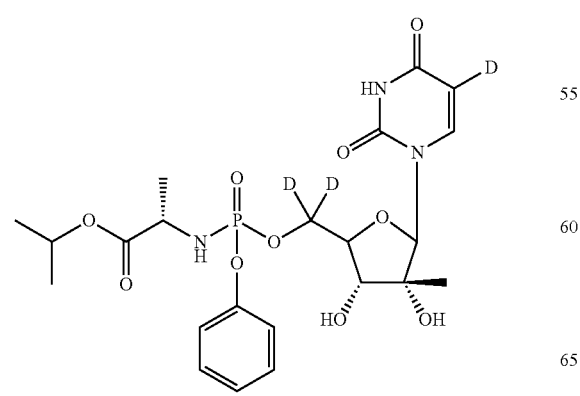

Formula IIA

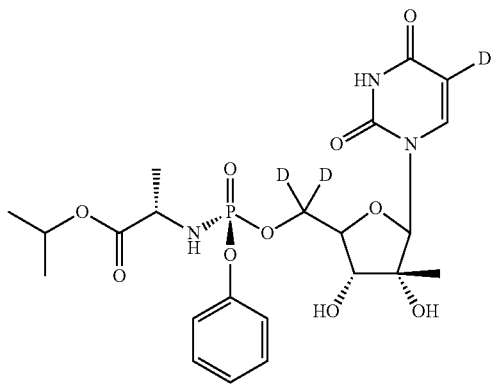

Formula IIB

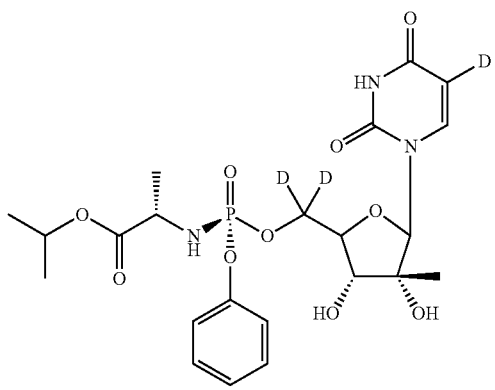

Formula IIIA

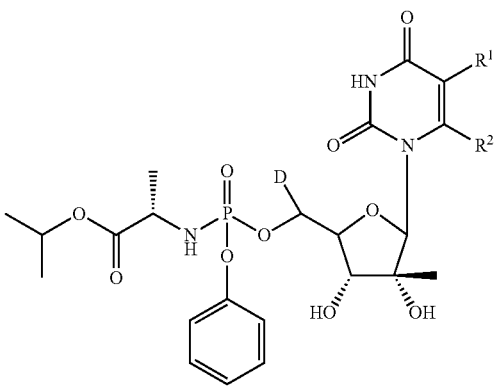

Formula IIIB

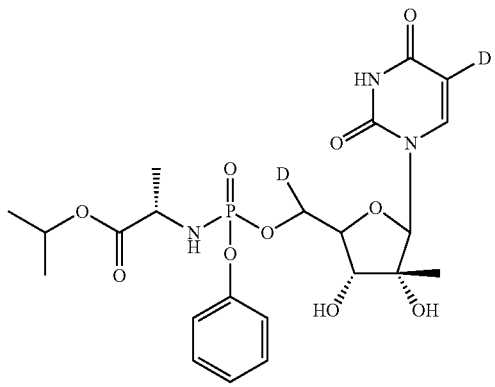

Therefore, in one embodiment a method for the treatment of a host infected with hepatitis C or another disorder described herein is provided that includes the administration of an effective amount of a compound of Formula I or II, or a pharmaceutically acceptable salt thereof, optionally in a pharmaceutically acceptable carrier.

In another embodiment, the nucleoside derivative of Formula I, II, IIIA, or IIIB is administered as a phosphorus R or S stereoisomer, which is at least in 90% pure form, and typically, 95, 98 or 99% pure form.

An embodiment also includes a nucleoside derivative of Formula I, II, IIIA, or IIIB, which is administered as a mixture phosphorus R or S stereoisomers, for example a 50/50 mixture. For example a mixture, such as a 50/50 mixture, of Formula IIA and IIB may be administered.

In another embodiment, an effective amount of a compound of the Formula IIIA or IIIB or its pharmaceutically acceptable salt, optionally in a pharmaceutically acceptable carrier, is provided to a host in need of hepatitis C therapy.

On administration to the host, for example, the phosphoramidate of Formula II is metabolized to the 5'-OH, 5'-D, D-monophosphate (Formula V) via a series of enzymatic steps.

Formula II, for example, is converted to its active species, the nucleoside triphosphate (Formula IV), via the nucleoside monophosphate (Formula V). Alternatively, the nucleoside monophosphate (Formula V) can undergo dephosphorylation to 5'-deuterated 2'-C-methyl uridine (Formula VI). The 5'-deuterated nucleoside triphosphate (Formula IV) is the pharmacologically active metabolite that inhibits hepatitis C viral replication, whereas the 5'-deuterated 2'-C-methyl uridine (Formula VI) shows little activity because it is a poor substrate for nucleoside monophosphate kinase.

5'-Deuterated nucleoside monophosphate (Formula V) if dephosphorylated will produce 5'-deuterated nucleoside (Formula VI) and the non-deuterated nucleoside monophosphate (Formula VIII) will produce undeuterated 2'-C-methyluridine (Formula IX).

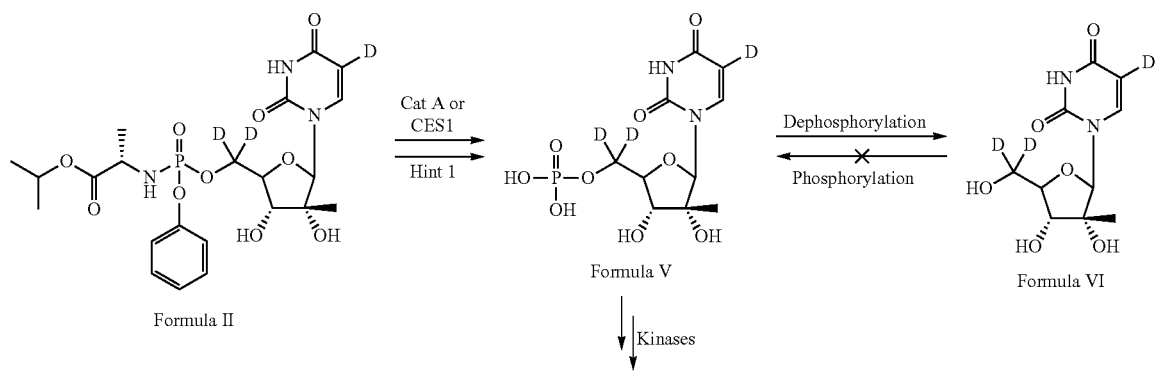

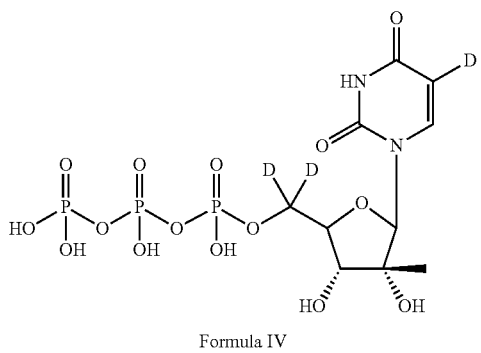

Formula IV

Cat A: Cathepsin A
CES1: Carboxlyesterase 1

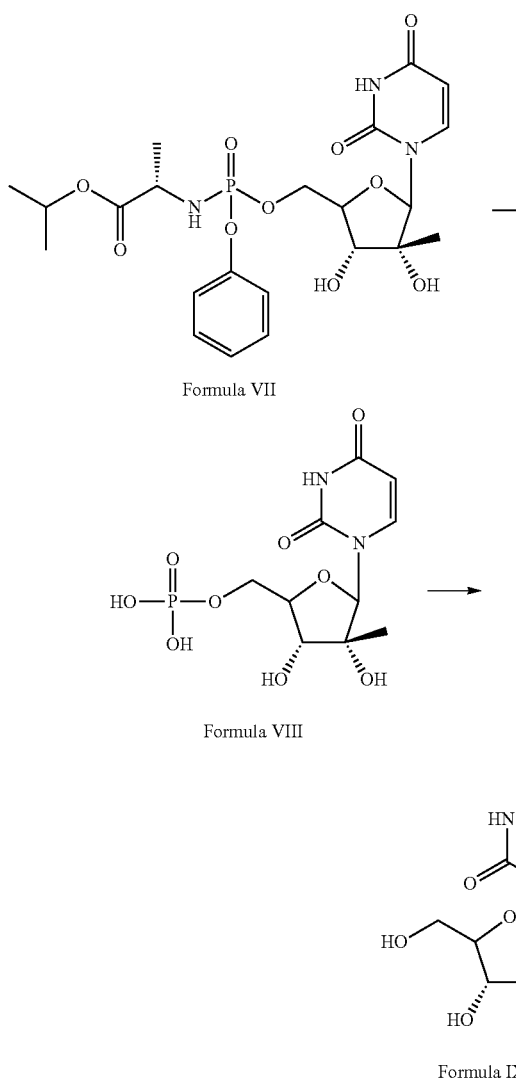

Formula VII

Formula VIII

Formula IX

It has surprisingly been discovered that deuterium in the 5'-position of the nucleoside stabilizes the nucleoside derivative from dephosphorylation to the undesired 5'-OH, 5'-deuterated-nucleoside. This is surprising because the deuterium atom(s) are not cleaved during dephosphorylation and are not bound to an atom that is cleaved during dephosphorylation. The disclosure includes the use 5'-deuterium to produce a significant effect on metabolism and efficacy through a remote and unexpectedly important secondary deuterium isotope effect. Such an important secondary deuterium isotope effect on de-monophosphorylation at the 5'-position has not been previously reported. By increasing the stability of the 5'-monophosphate of the nucleoside against dephosphorylation, an increase in the active 5'-triphosphate pool of the nucleoside can be achieved, which can result in increased efficacy at a given oral dosage or equal efficacy using a lower dose of the nucleoside in the clinic. It may also have a significant effect on the half-life, and thus pharmacokinetics, of the drug.

Therefore, in another embodiment, the present disclosure includes a method for treating a host afflicted with a disorder that is treatable with a nucleoside or nucleotide, the improvement comprising substituting one or both of the hydrogens at the 5'-position of the nucleoside or nucleotide with a deuterium with at least 90% enrichment over protium (i.e., less than 10% $^1$H hydrogen) (and in other embodiments, 50, 95, 98 or 99% enrichment). The therapeutic effect of any nucleotide or nucleoside can be enhanced if the active metabolite is the mono, di or triphosphate of the nucleoside by 5'deuteration of the nucleoside, because 5'-deuteration increases the pool of the nucleoside monophosphate. Nucleoside monophosphate is metabolized to the diphosphate and/or triphosphate with the corresponding nucleoside diphosphate kinase and then nucleoside triphosphate kinase. This method is especially useful for nucleosides which are not easily monophosphorylated, and thus lose substantial activity when dephosphorylated, that cannot be easily recovered by the action of nucleoside monophosphate kinase.

In one embodiment, the disorder is a viral disease. In another embodiment, the disorder is hepatitis B or C. In yet another embodiment, the disorder is HIV. In another embodiment, the disorder is abnormal cellular proliferation. In yet another embodiment, the disorder is a tumor or cancer. The nucleoside derivative used in this improved method can, for example, be a phosphoramidate or other stabilized nucleotide prodrug that is metabolized to the 5'-monophosphate, or can be the 5'-monophosphate itself. In one embodiment, the nucleoside derivative contains a 2'-α-methyl, 2'-β-hydroxy nucleoside. In yet another embodiment, the nucleoside derivative contains a 2'-α-methyl, 2'-β-fluoro nucleoside. In optional embodiments, the methyl group can have one or more halogens, for example, fluorine(s).

Nucleoside triphosphate (NTP) is the active species that inhibits viral replication in hepatocytes and its levels and intrinsic potency drive the effectiveness of the treatment.

A demonstration of the increase in critical nucleoside triphosphate levels caused by the use of 5'-deuteration is provided in Example 13 below. In this Example, the compound of Formula II as well as the corresponding undeuterated compound (Formula VII) were incubated in fresh liver hepatocytes for 24 hours. The data show that there is more dephosphorylated nucleoside (i.e., undesired 5'-OH nucleoside) in the samples incubated with the undeuterated phosphoramidate than with the 5'-deuterated phosphoramidate. Specifically, using 20 µM Formula II or its undeuterated counterpart Formula VII (12 well plate (1 ml) with hepatocytes seeded at 0.67 million cells per well for 24 hours) results in a 1.9 fold (media, i.e., extracellular concentration) and 2.9 fold (cell extract, i.e., intracellular) higher concentration of undeuterated dephosphorylated 2'-methyl uridine (Formula IX) compared to that resulting from the 5'-deuterated form (Formula VI). Results of incubation of 20 µM Formula II or its undeuterated counterpart (Formula VII) (6 well plate (2 ml) with hepatocytes seeded at 1.7 million cells per well for 24 hours) indicate a 1.5 fold (cell extract, i.e., intracellular) and 2.8 fold (cell extract, i.e., intracellular) higher concentration of undeuterated dephosphorylated 2'-methyl uridine (Formula IX) compared to that resulting from the 5'-deuterated form (Formula VI). Thus on average, the dephosphylation in hepatocytes leads to about twice as much 5'-OH-nucleoside produced when the 5'-position is not deuterated. This difference in 5'-monophosphate pool (such as Formula VIII for the undeuterated version) available for activation to the triphosphate when 5'-deuterated phosphoramidate is used can have a significant effect on efficacy, dosage, toxicity and/or pharmacokinetics of the drug.

As a comparison to a clinical trial candidate as further described in Example 14 and FIG. 3, a poster presented by Alios (EASL 2013) indicates that the level of VX-135 triphosphate measured in human hepatocytes after 24 hours incubation with 50 µM VX-135 was 1174 pmol/million cells. In contrast, the level of Formula IV after 25 hours of incubation of human hepatocytes with 5 µM of Formula II, i.e., a ten times lower concentration, is 486 pmol/million cells. Therefore, the amount of triphosphate produced by incubation of Formula II is 4-fold greater (does-normalized) than the amount of triphosphate produced by VX-135. While the precise structure of VX-135 is not currently known, it is a uridine nucleotide analog prodrug NS5B inhibitor.

In addition, after incubation of Formula II at 50 nM in primary hepatocytes for 24 hrs, the level of Formula IV ranged 9.2-16.2 pmol/million cells. These concentrations are 5- to 8-fold higher than those obtained when the Huh-luc/neo cells were incubated at 50 nM. Since Formula IV is the active species which inhibits HCV replicon replication in Huh-luc/neo cells, the predicted $EC_{50}$ of Formula II in primary human hepatocytes would be 6.25-10 nM if HCV replicon could grow in primary hepatocytes, presuming the linear relationship obtained in FIG. 1 between Formula II and Formula IV continues at lower concentration.

As detailed in Example 14 and Table 4, the half-life of Formula IV is greater than the half-life of the triphosphate of Sovaldi in hepatocytes from four species. The longest half-life was in human hepatocytes, followed by dog, then monkey and then rat. The half-lives range from 10-30 hours for Formula IV and 8-23 hours for the triphosphate of Sovaldi.

Further, as described in Example 17 and FIGS. 2 and 3, over a 48 hour period, while the intracellular conversion to the corresponding triphosphate of Sovaldi (GS-7977) as measured in human hepatocytes is 2-fold greater than that of the triphosphate derived from Formula II (i.e., Formula IV), the concentration of Formula IV is still increasing at 48 hours, while the concentration of the triphosphate metabolite of Sovaldi decreases from 24 to 48 hours. The increasing concentration of Formula IV, combined with its half-life of >24 h, suggest accumulation of Formula IV (the triphosphate of Formula II) levels in hepatocytes on repeat dosing. This trend, after an initial in vivo initial dosing ramp up acclimation, can lead to a higher steady state concentration of Formula IV in vivo for the triphosphate derived from Formula II than the triphosphate of Sovaldi. In addition, the intrinsic potency (the inhibitory effect on the RdRp activity of NS5B) of Formula IV (the triphosphate of Formula II) is 1.5 fold better than the intrinsic potency of the triphosphate of Solvadi.

The disclosure also includes a method of treating an HCV infection or a related disorder in a patient, comprising providing a therapeutically effective amount of one or more of the active compounds described herein, optionally in combination or alternation with one or more other anti-HCV active agents or other medical therapies that have additive or synergistic benefit for the patient.

DETAILED DESCRIPTION

Chemical Description and Terminology

Figure 1:
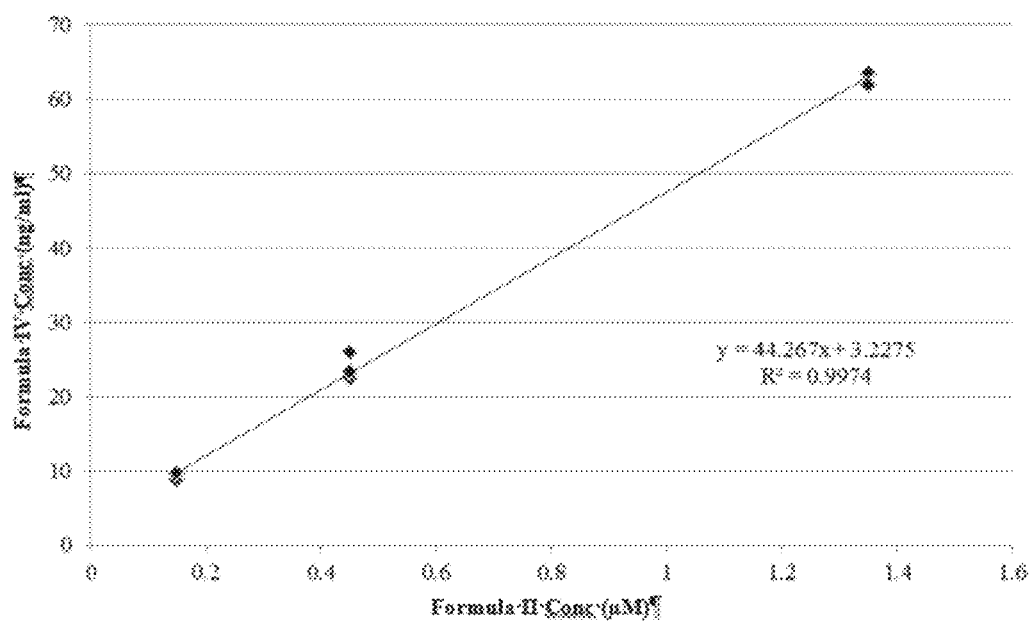
FIG. 1 is a graph of the concentration of Formula IV (ng/ml) vs. concentration of Formula II (µM) in human liver hepatocytes. Formula IV concentrations in human hepatocytes were determined after 24 hour incubations with 0.15, 0.45, and 1.35 µM Formula II.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

Compounds of Formula I include other formulae disclosed herein within the scope of Formula I. These include, for example, compounds of Formula II, IIA, IIB, and compound 22.

Compounds of Formula I include compounds of the formula having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$. Compounds of Formula I also require enrichment of deuteration (substitution of a hydrogen atom with deuterium) at identified positions.

An "active agent" is a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

The term "substituted", as used herein, means that any one or more hydrogens on the designated atom or group is replaced with a selection from the indicated group, provided that the designated atom's normal valence is not exceeded.

Deuteration" and "deuterated" mean that a hydrogen at the specified position is replaced by deuterium. In any sample of a compound of Formula I in which a position is deuterated some discrete molecules of the compound of Formula I will likely have hydrogen, rather than deuterium, at the specified position. However the percent of molecules of the compound of Formula I in the sample which have deuterium at the specified position will be much greater than would naturally occur. The deuterium at the deuterated position is enriched. The term "enriched" as used herein, refers to the percentage of deuterium versus other hydrogen species at that location. As an example, if it is said that a position in the compound of Formula I contains 50% deuterium enrichment, that means that rather than hydrogen at the specified position the deuterium content is 50%. For clarity, it is confirmed that the term "enriched" as used herein does not mean percentage enriched over natural abundance. In one embodiment, deuterated compounds of Formula I will have at least 10% deuterium enrichment at any deuterated position. In other embodiments, there will be at least 50%, at least 90%, or at least 95% deuterium enrichment at the specified deuterated position or positions. A "deuterated substituent" is a substituent in which at least one hydrogen is replaced by deuterium at the specified percent enrichment. "Optionally deuterated" means that the position may be either hydrogen and the amount of deuterium at the position is only the naturally occurring level of deuterium or the position is enriched with deuterium above the naturally occurring deuterium level.

A "dosage form" means a unit of administration of an active agent. Non-limiting examples of dosage forms include tablets, capsules, injections, suspensions, liquids, intravenous fluids, emulsions, creams, ointments, suppositories, inhalable forms, transdermal forms, and the like.

"Aryl" indicates aromatic groups containing only carbon in the aromatic ring or rings. Aryl groups include, for example, phenyl and naphthyl, including 1-naphthyl and 2-naphthyl.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups. It is preferred that the total number of S and O atoms in the heteroaryl group is not more than 2 Examples of heteroaryl groups include, thienyl pyridyl, pyrimidinyl, and pyrrolyl.

"Heterocycloalkyl" is a saturated ring group, having 1, 2, 3, or 4 heteroatoms independently chosen from N, S, and O, with remaining ring atoms being carbon. Monocyclic heterocycloalkyl groups typically have 4 to 6 ring atoms. Examples of heterocycloalkyl groups include morpholinyl, piperazinyl, piperidinyl, and pyrrolinyl.

"Pharmaceutical compositions" are compositions comprising at least one active agent, such as a compound or salt of one of the active compounds disclosed herein, and at least one other substance, such as a carrier. Pharmaceutical compositions optionally contain one or more additional active agents. "Pharmaceutical combinations" or "combination therapy" refers to the administration of at least two active agents which may be combined in a single dosage form or provided together in separate dosage forms optionally with instructions that the active agents are to be used together to treat a disorder, such as hepatitis C, or a disorder associated with hepatitis C, or another viral infection as described herein "Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. The pharmaceutically acceptable salt can be in the form of a pure crystal, or single polymorphic form, or can be used in non-crystalline or amorphic, glassy, or vitreous form, or a mixture thereof. In an alternative embodiment, the active compound can be provide in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations means a diluent, excipient, or vehicle with which an active compound is provided.

A "pharmaceutically acceptable excipient" means an excipient that is useful in preparing a pharmaceutical composition/combination that is generally safe, is sufficiently non-toxic, and neither biologically nor otherwise undesirable. A "pharmaceutically acceptable excipient" as used in the present application includes both one and more than one such excipient.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. In certain embodiments a therapeutically effect amount is thus an amount sufficient to provide a significant reduction in elevated AST and ALT levels or an amount sufficient to provide a return of AST and ALT levels to within the normal range. A therapeutically effective amount is also alternatively an amount sufficient to prevent a significant increase or significantly reduce the detectable level of virus or viral antibodies in the patient's blood, serum, or tissues. One method of determining treatment efficacy includes measuring HCV RNA levels by a conventional method for determining viral RNA levels such as the Roche TaqMan assay. In certain preferred embodiments treatment reduces HCV RNA levels below the limit of quantitation (30 IU/mL, as measured by the Roche TaqMan (R) assay) or more preferably below the limit of detection (10 IU/mL, Roche TaqMan).

A "patient" or "host" is a human or non-human animal in need of medical treatment. Medical treatment can include treatment of an existing condition, such as a disease or disorder, prophylactic or preventative treatment, or diagnostic treatment. Unless otherwise stated, the patient or host is a human patient.

Highly Active Nucleoside Derivatives

It has been surprisingly discovered that the 2'-methyl 5'-deuterated uridine phosphoramidate of Formula I, including Formula II, or Formula IIIA or IIIB, or a pharmaceutically acceptable salt thereof, wherein deuterium has an enrichment over protium of at least 90% (i.e., less than 10% $^1$H hydrogen), and wherein $R^1$ and $R^2$ are independently deuterium or hydrogen, is a superior NS5B inhibitor for the treatment of hepatitis C, or any other disorder disclosed herein. In one embodiment, $R^1$ is deuterium and $R^2$ is hydrogen.

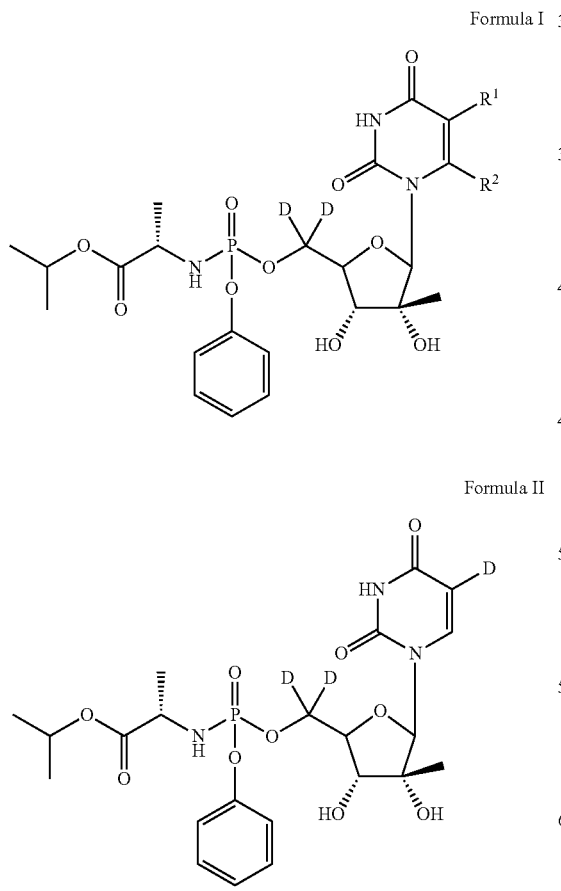

Formula I

Formula II

Formula II comprises mixtures of stereoisomers. For example Formula II includes a 50/50 mixture of stereoisomers of Formula II, wherein the mixture comprises

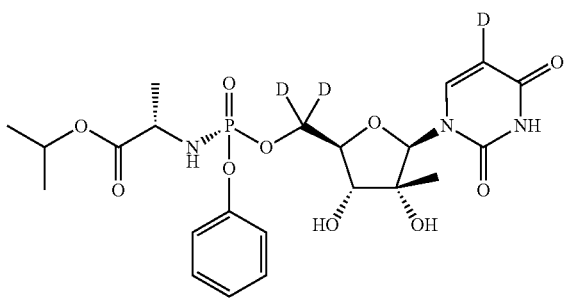

and

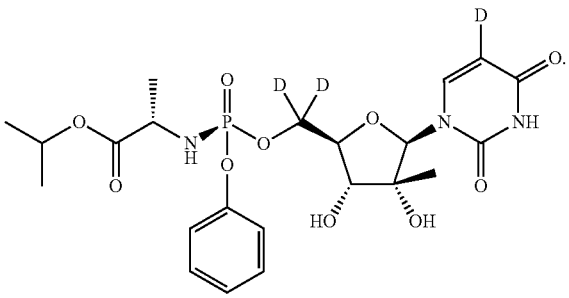

Therefore, in one embodiment a method for the treatment of a host infected with hepatitis C or related disorder as described herein, is provided that includes the administration of an effective amount of a compound of Formula I or II, or a pharmaceutically acceptable salt thereof, optionally in a pharmaceutically acceptable carrier.

In an alternative embodiment, one or both of the 5'-deuterium(s) independently represents at least 50% enrichment. In another embodiment, the enrichment is independently at least 75% or 80%. In another embodiment, one or both of the 5'-deuterium(s) independently represents at least 90%, 95% or 98% enrichment.

In another embodiment, the nucleoside derivative of Formula I or II is administered as a phosphorus R or S stereoisomer, which is at least in 90% pure form, and typically, 95, 98 or 99% pure form, or which is administered as a mixture of phosphorous chiral center stereoisomers, such as a 50/50 mixture of phosphorous chiral center stereoisomers, or a mixture in which the ratio of R to S stereoisomers at the phosphorous chiral center is from 10:90 to 90:10 or from 30:70 to 70:30.

In another embodiment, an effective amount of a compound of the Formula IIIA or IIIB or its pharmaceutically acceptable salt, optionally in a pharmaceutically acceptable carrier, is provided to a host in need of hepatitis C therapy, or another therapy as disclosed herein.

Formula IIIA

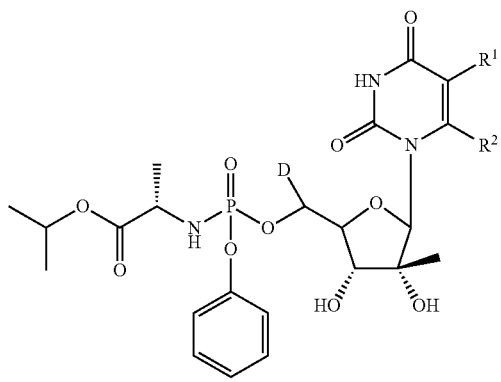

Formula IIIB

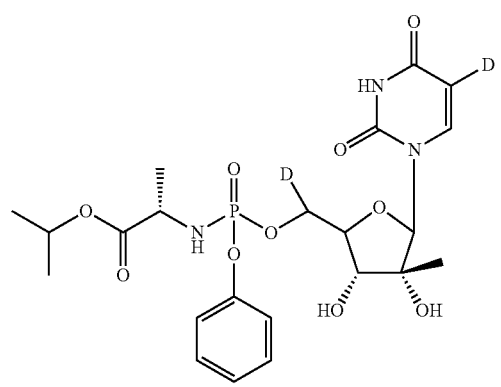

It has surprisingly been discovered that deuterium in the 5'-position of the nucleoside stabilizes the nucleoside derivative from dephosphorylation to the undesired 5'-OH, 5'-deuterated-nucleoside. This is surprising because the deuterium atom(s) are not cleaved during dephosphorylation and are not bound to an atom that is cleaved during dephosphorylation. Therefore, 5'-deuterium can producing a significant effect on metabolism and efficacy through a remote and unexpectedly important secondary deuterium isotope effect. Such an important secondary deuterium isotope effect on de-monophosphorylation at the 5'-position has not been reported previously in the literature. By increasing the stability of the 5'-monophosphate of the nucleoside against dephosphorylation, an increase in the active 5'-triphosphate pool of the nucleoside is achieved, which can result in increased efficacy at a given oral dosage or equal efficacy using a lower dose of the nucleoside. It may also have a significant effect on the half-life, and thus pharmacokinetics, of the drug.

The present disclosure provides a significant improvement over the compounds disclosed in U.S. Patent Application Publication US 2012/0071434; U.S. Ser. No. 13/36, 435), published Mar. 22, 2012 and assigned to Alios BioPharma, Inc. which describes phosphorothioamidate nucleosides for the treatment of viral diseases. It is known that the replacement of oxygen with sulfur in a nucleoside 5'-phosphate stabilizes the phosphate against nucleotidase or other hydrolyzing action, which forms the basis for the use of phosphorothioates and other thiophosphate derivatives in antisense and aptamer stabilization chemistry which was developed in the 1980's. See generally, among other references, Pearson, "Characterization of ectonucleotidases on vascular smooth-muscle cells", Biochem J. (1985), 230, 503-507. One of the compounds disclosed by Alios is:

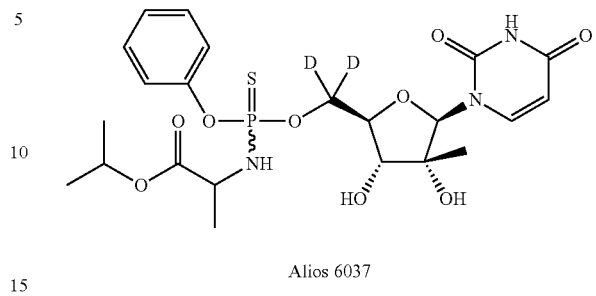

Alios 6037

The monothiophosphate metabolite which would result from the cleavage of the phosphorothioamidate 6037 in vivo would be stabilized from further enzymatic breakdown to the free 5'-hydroxyl nucleoside due to the presence of the stabilizing, unnatural sulfur atom. Therefore, the stabilizing effect of deuteration at the 5'-position is masked by the sulfur. Further, it is also known that nucleoside monothiophosphates are hydrolyzed to nucleoside monophosphates via the Hintl enzyme (the enzyme that is also responsible for production of monophosphate Formula V as well as monothiophosphates from their respective prodrugs), releasing $H_2S$, which can cause physiological and pathogenic effects (see Ozga et al. J. Biol. Chem. 2010, 285, 40809).

A significant improvement provided by the present invention is the surprising discovery that 5'-deuteration using a more natural phosphoramidate, i.e., without sulfur, protects the monophosphate from further breakdown to the free hydroxyl group in a manner that minimizes toxicity and more closely mimics natural compounds. The fact that this is a nonobvious invention is dramatically highlighted with a review of U.S. Publication 2011/0251152 (U.S. Ser. No. 13/076,552), assigned to Pharmasset, Inc., the company that developed Sovaldi. On page 16 of the publication, this nucleoside-experienced company described the use of deuteration in six different species of Sovaldi, but never considered placing the deuterium in the 5'-position, now determined to be the most important position.

Methods of Treatment

The disclosure provides a method to treat a host, typically a human, infected with hepatitis C, or another disorder described herein, with an effective amount of one of the highly active nucleoside derivatives of Formula I, optionally as a pharmaceutically acceptable salt and optionally in a pharmaceutically acceptable carrier.

In another embodiment, an effective amount of one of the highly active nucleoside derivatives described herein, optionally as a pharmaceutically acceptable salt and optionally in a pharmaceutically acceptable carrier can be used to treat a host, typically a human, with a secondary condition associated with hepatitis C, including but not limited to those disorders described below in (i) through (viii).

This disclosure provides methods of treating a viral infection in a patient, including a hepatitis C infection, by providing an effective amount of a compound or pharmaceutically acceptable salt of Formula I to the patient infected with a hepatitis C virus. A compound or salt of Formula I may be provided as the only active agent or may be provided together with one or more additional active agents. In certain embodiments the compound or salt of Formula I is administered together with a NS3 protease inhibitor, a NS5A inhibitor, a NS5B inhibitor, or a combination of the foregoing.

An effective amount of a pharmaceutical composition/combination of the disclosure may be an amount sufficient to (a) inhibit the progression of hepatitis C; (b) cause a regression of the hepatitis C infection; or (c) cause a cure of a hepatitis C infection such that HCV virus or HCV antibodies can no longer be detected in a previously infected patient's blood or plasma. An amount of a pharmaceutical composition/combination effective to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

In yet another embodiment, an effective amount of one of the highly active nucleoside derivative described herein, optionally as a pharmaceutically acceptable salt and optionally in a pharmaceutically acceptable carrier can be used as a prophylaxis to ward off or prevent a host, typically a human, having a hepatitis C infection lead to a secondary condition associated with hepatitis C. In an alternative embodiment, an effective amount of one of the highly active nucleoside derivatives described herein, optionally as a pharmaceutically acceptable salt, and optionally in a pharmaceutically acceptable carrier can be used to treat a secondary condition associated with hepatitis C including but not limited to those disorders described below in (i) through (viii)

(i) Cryoglobulinemia which is the production of abnormal antibodies (called cryoglobulins) due to hepatitis C virus stimulation of lymphocytes. These antibodies can deposit in small blood vessels, thereby causing inflammation of the vessels (vasculitis) in tissues throughout the body including the skin, joints and kidneys (glomerulonephritis).

(ii) B-cell non-Hodgkin's lymphoma associated with hepatitis C, which is considered to be caused by excessive stimulation by hepatitis C virus of B-lymphocytes, resulting in abnormal reproduction of the lymphocytes.

(iii) Skin conditions such as lichen planus and porphyria cutanea tarda have been associated with hepatitis C infection.

(iv) Cirrhosis, which is a disease in which normal liver cells are replaced with scar or abnormal tissue. Hepatitis C is one of the most common causes of liver cirrhosis.

(v) Ascites, which is the accumulation of fluid in the abdominal cavity commonly caused by cirrhosis of the liver, which can be caused by hepatitis C infection.

(vi) Hepatocellular carcinoma, of which 50% of the cases in the U.S. are currently caused by chronic hepatitis C infection.

(vii) Hepatitis C related jaundice, which is a yellowish pigmentation caused by increased bilirubin.

(viii) Thrombocytopenia is often found in patients with hepatitis C and may be the result of bone marrow inhibition, decrease in liver thromopoietin production and/or an autoimmune mechanism. In many patients, as hepatitis C advances, the platelet count decreases and both bone marrow viral inhibition and antiplatelet antibodies increase. Other symptoms and disorders associated with hepatitis C that may be treated by an effective amount of a pharmaceutical composition/combination of the disclosure include decreased liver function, fatigue, flu-like symptoms: fever, chills, muscle aches, joint pain, and headaches, nausea, aversion to certain foods, unexplained weight loss, psychological disorders including depression, and tenderness in the abdomen.

The active compounds presented herein can also be used to enhance liver function generally associated with hepatitis C infection, for example. synthetic function including synthesis of proteins such as serum proteins (e.g., albumin, clotting factors, alkaline phosphatase, aminotransferases (e.g., alanine transaminase, aspartate transaminase), 5'-nucleosidase, glutaminyl transpeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

The pharmaceutical compositions/combinations disclosed herein are also useful for treating viral infections in patients other than a hepatitis C infection. In an alternative embodiment, the infection may be an RNA viral infection, such as Togaviridae, Picornaviridae, Coronaviridae, or Flaviviridae viral infection. The disclosure includes a method of treating a Togaviridae, Picornaviridae, Coronaviridae, or Flaviviridae viral infection by administering an effective amount of one of the active compounds disclosed herein, to a subject infected with a togavirus, picornavirus, coronavirus, or flavivirus. Flaviviridae viral infections include infections with viruses of the genera *Flavivirus, Pestivirus*, and *Hepacivirus. Flavivirus* infections include yellow fever, Dengue fever, West Nile virus, encephalitis, including St. Louis encephalitis, Japanese B encephalitis, California encephalitis, central European encephalitis, Russian spring-summer encephalitis, and Murray Valley encephalitis, Wesselsbron disease, and Powassan disease. *Pestivirus* infections include primarily livestock diseases, including swine fever in pigs, BVDV (bovine viral diarrhea virus) in cattle, and Border Disease virus infections. *Hepacivirus* infections include Hepatitis C and canine *Hepacivirus*. Togavirus infections include *Sindbis* virus, Eastern equine encephalitis virus, Western equine encephalitis virus, Venezuelan equine encephalitis virus, Ross River virus, O'nyong'nyong virus, Chikungunya virus, Semliki Forest virus, and *Rubella* virus. Picornavirus infections include infections with viruses of the genuses *Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Salivirus, Sapelovirus, Senecavirus, Teschovirus*, and *Tremovirus*. Coronavirus infections include infections with virus of the genuses *Alphacoronavirus, Betacoronavirus* (which includes Severe acute respiratory coronavirus (SARS)), *Gammacoronavirus*, and *Deltacoronavirus*. The disclosure particularly includes compositions comprising a compound of the present disclosure useful for treating Dengue fever, West Nile fever, yellow fever, or BVDV (bovine viral diarrhea virus) and methods of treating these infections by administering the compound to a patient infected with the virus.

The disclosure also includes the following methods of treatment: (i) A method for treating a host afflicted with hepatitis C comprising administering an effective treatment amount of a nucleoside or nucleotide that has deuterium with at least 50% enrichment at the 5'-position of the nucleoside or nucleotide. (ii) A method of treatment as in method (i) wherein the nucleotide is not a thiophosphate or thiphosphate prodrug. (iii) A method for the treatment of a host afflicted with a disorder that can be treated with an effective amount of a nucleoside or nucleotide, the improvement comprising administering the nucleoside or nucleotide as a 5'-deuterated nucleoside or nucleotide. (iv) A method of treatment as in (i) wherein the nucleotide is not a thiophosphate or thiphosphate prodrug. (v) A method of treatment as in (i), wherein the enrichment is at least 90%. (vi) A method of treatment as in (i), wherein there are two deuteriums at the 5'-position. (vii) A method of treatment as in (iii), wherein the nucleotide is not a thiophosphate or thiphosphate prodrug. (viii) A method of treatment as in (iii), wherein the enrichment is at least 90% (viii) The method of claim 23, wherein there are two deuteriums at the 5'-position.

Combination Therapy

The present disclosure also includes pharmaceutical compositions and combinations comprising an active compound described herein and at least on additional active agent, as well as methods of treatment comprising administering such compositions to a patient infected with hepatitis C, or another disorder described herein. In certain embodiments the additional active agent is an HCV NS3 protease inhibitor or an HCV NS5A or another NS5B inhibitor.

In nonlimiting embodiments, the active HCV compound of the present disclosure can be administered in combination or alternation with one or more of the active compound that is a caspase inhibitor, a cyclophilin inhibitor, a cytochrome P450 monooxygenase inhibitor, an entry inhibitor, a glucocorticoid, an HCV protease inhibitor, a hematopoietin, a homeopathic therapy, an immunomodulatory compound, an immunosuppressant, an interleukin, an interferon or interferon enhancer, an IRES inhibitor, a monoclonal or polyclonal antibody, a nucleoside or nucleotide analogue or prodrug, a non-nucleoside inhibitor, an NS4B inhibitor, an NS5A inhibitor, an NS5B inhibitor, a P7 protein inhibitor, a polymerase inhibitor, an RNAi compound, a therapeutic vaccine, a TNF agonist, a tubulin inhibitor, a sphingosine-1-phosphate receptor modulator, or a TLR agonist.

Nonlimiting examples of active agents in these categories are:

Caspase Inhibitors: IDN-6556 (Idun Pharmaceuticals)

Cyclophilin Inhibitors: for example, NIM811 (Novartis), SCY-635 (Scynexis), and DEBIO-025 (Debiopharm);

Cytochrome P450 monooxygenase inhibitors: ritonavir, ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, and VX-497 (Merimebodib). Preferred CYP inhibitors include ritonavir, ketoconazole, troleandomycin, 4-methyl pyrazole, cyclosporin, and clomethiazole;

Entry Inhibitors: ITX-5061 (iTherX)

Glucocorticoids: hydrocortisone, cortisone, prednisone, prednisolone, methylprednisolone, triamcinolone, paramethasone, betamethasone, and dexamethasone.

HCV Protease Inhibitors: for example Sovaprevir and ACH-2684. ABT-450 (Abbott), ACL-181 and AVL-192 (Avila), BMS-032 (Bristol Myers Squibb), Boceprevir (Merck), danoprevir (Hoffman-La Roche and Genentech), GS-9256 (Gilead), GS-9451 (Gilead), Telaprevir (VX-950, Vertex), VX-985 (Vertex), Simeprevir (TMC435, Tibotec), Fosamprenavir (prodrug of Amprenavir, Glaxo/Vertex), indinavir (CRIXIVAN, Merck), TMC435350 (Tibotec/Medivir), Faldaprevir (BI 201335. Boehringer Ingelheim), PHX-1766 (Phenomix), Vaniprevir (MK-7009, Merck), narlaprevir (SCH900518, Schering), MK-5172 (Merck)

Hematopoietins: hematopoietin-1 and hematopoietin-2. Other members of the hematopoietin superfamily such as the various colony stimulating factors (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha-nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Ares-Serono, Inc. and Pfizer), consensus interferon alpha (INFERGEN, Intermune), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.), and lamdba interferon (BMS)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (HEPX-C, XTL), HuMax-HepC (Genmab), Hepatitis C Immune Globin (human) (CIVACIR, Nabi Biopharmceuticals), XTL-002 (XTL), Rituximab (RITUXAN, Genentech/IDEC), GS-6624 (Gilead)

Nucleoside analogues: Sofosbuvir (PSI-7977, Pharmasset and Gilead), PSI-7851 (Pharmasset), PSI-7977 (Pharmasset), R7128 (mericitabine, Roche), R7348 (Roche), NM283 (valopicitabine, Idenix), GS-6620 (Gilead), TMC-649 (Tibotec), VX-135 (Vertex, Alios), ALS-2200 (Alios), IDX184 (Idenix), IDX21437 (Idenix), IDX21459 (Idenix), Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), isatoribine (Anadys Pharmaceuticals), ANA245 (Anadys Pharmaceuticals), and viramidine (ICN), an amidine prodrug of ribavirin. Combinations of nucleoside analogues may also be employed.

Non-nucleoside inhibitors: PSI-6130 (Roche/Pharmasset), ABT-333 and ABT-072 (Abbott), delaviridine (RE- SCRIPTOR, Pfizer), PF-868554 (Pfizer), GSK-852 (GlaxoSmithKline), Setrobuvir (ANA-598, Anadys), VX-222 (Vertex), BI-127 (Boehringer Ingelheim), and BMS-325 (Bristol Meyers)

NS4B inhibitors: clemizole (Eiger BioPharmaceuticals, Inc.)

NS5A inhibitors: Daclatasvir (BMS-790052, BMS), AZD-729 (Astra Zeneca); PPI-461 (Presidio), PPI-688 (Presidio), samatasvir (IDX719, Idenix), ledipasvir (GS-5885, Gilead), GS-5816 (Gilead), ombitasvir (ABT-267, AbbVie), GSK2336805 (GlaxoSmithKline), and elbasvir (MK-8742, Merck).

Tubulin inhibitors: Colchicine

Sphingosine-1-phosphate receptor modulators: FTY720 (Novartis)

TLR agonists: TLR7 agonist (Anadys Pharmaceuticals), CPG10101 (Coley), and TLR9 agonists including CPG 7909 (Coley).

Vaccines: HCV/MF59 (Chiron), IC41 (Intercell)

For example, in some embodiments, the additional active agent is sovaprevir or ACH-2684 (HCV NS3 protease inhibitors) and/or and NS5a inhibitor.

The disclosure includes compositions in which the additional active agent is

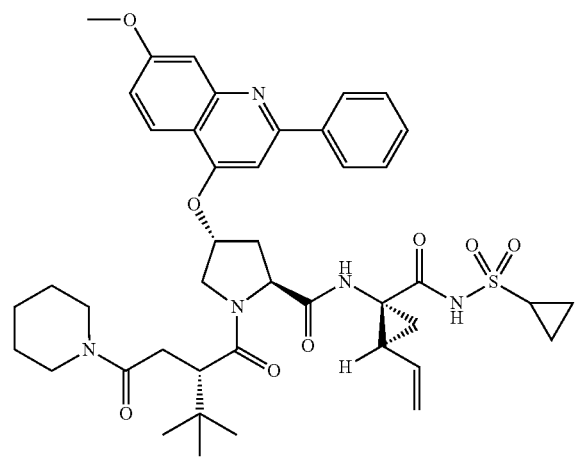

Sovaprevir

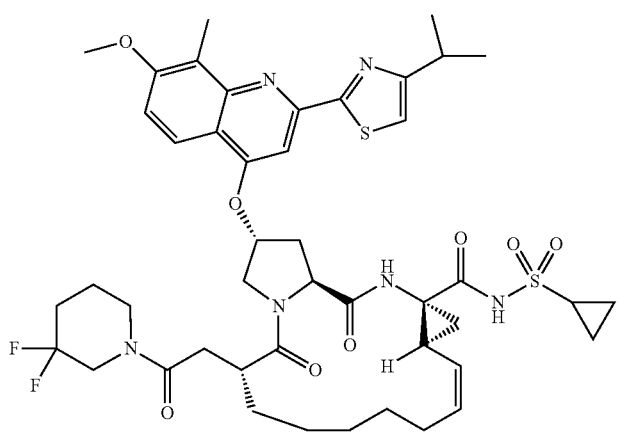

ACH-2684

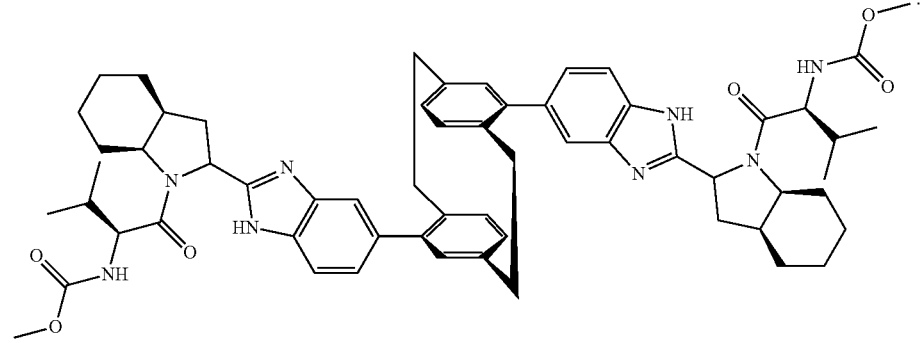

NS5A inhibitor

NS5B inhibitors: MBX-700 (Microbotix/Merck), RG-9190, VX-222 (Vertex), and BMS-791325 (Bristol Meyers Squibb).

P7 protein inhibitor: amantadine (SYMMETREL, Endo Pharmaceuticals, Inc.)

Polymerase inhibitors: ANA598 (Anadys), Tegobuvir (GS 9190, Gilead).

RNA interference: SIRNA-034 RNAi (Sirna Therapeutics)

Therapeutic Vaccines: IC41 (Intercell), GI 5005 (Globeimmune), Chronvac-C (Tripep/Inovio)

TNF agonists: adalimumab (HUMIRA, Abbott), entanercept (ENBREL, Amgen and Wyeth), infliximab (REMICADE, Centocor, Inc.)

NS3 protease inhibitors, useful in the pharmaceutical compositions and combinations described here have been disclosed previously, for example in U.S. Pat. No. 7,906,619, issued Mar. 15, 2011, is hereby incorporated by reference in its entirety for its teachings regarding 4-amino-4-oxobutanoyl peptides. The '619 patent is particularly incorporated by reference at the Examples section beginning in column 50 and extending to column 85 which discloses compounds useful in compositions/combination with Compounds of Formula I described here.

US Pat. Appl. No. 2010-0216725, published Aug. 26, 2010, is hereby incorporated by reference in its entirety for its teachings regarding 4-amino-4-oxobutanoyl peptides. The '725 application is particularly incorporated by reference at the Examples section beginning at page 22 and extending to page 100 which discloses compounds useful in compositions/combination with Compounds of Formula I described here.

Published US Pat. Appl. No. 2010-0152103, published Jun. 17, 2010, is hereby incorporated by reference in its entirety for its teachings regarding 4-amino-4-oxobutanoyl peptide cyclic analogues. The '103 application is particularly incorporated by reference at the Examples section beginning at page 19 and extending to page 60 which discloses compounds useful in compositions/combination with Compounds of Formula I and II described herein. Particularly the compounds of Formula I and II disclosed herein may be used in combination with an NS3 protease inhibitor of the formulae shown below.

NS5A inhibitors, useful in the pharmaceutical compositions and combinations described here have been disclosed previously. U.S. Pat. Pub. No. US-2012-0302528, published Nov. 29, 2012, is hereby incorporated by reference in its entirety for its teachings regarding NS5A Inhibitors.

In certain embodiments the deuterated nucleoside prodrug is

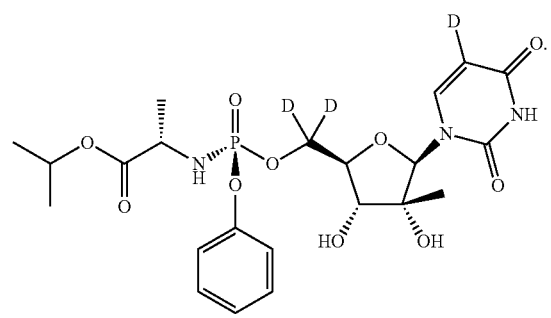 [SMILES: [2H]c1cn([C@@H]2O[C@H](C([2H])([2H])O[P@@](=O)(N[C@@H](C)C(=O)OC(C)C)Oc3ccccc3)[C@@H](O)[C@@]2(C)O)c(=O)[nH]c1=O]

The NS3 protease inhibitor is chosen from

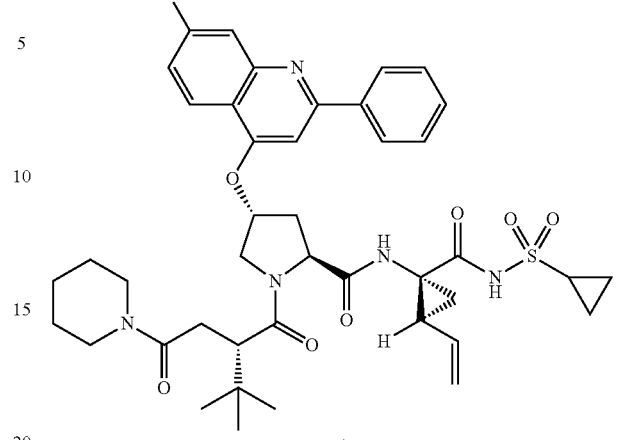

and

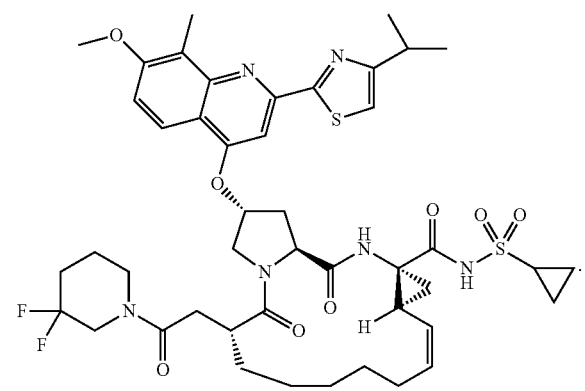

The NS5A inhibitor is chosen from

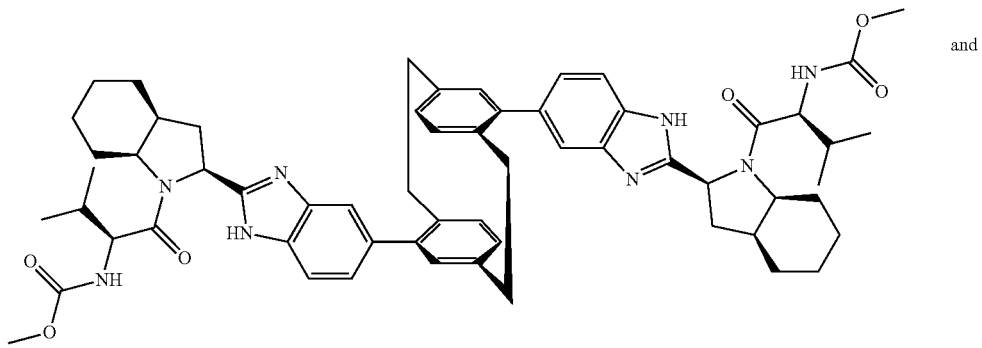

and

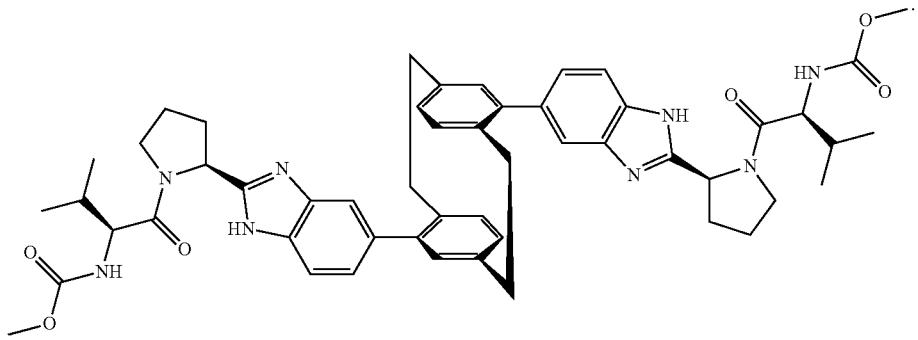

Pharmaceutical Compositions

Compounds disclosed herein can be administered as the neat chemical, but are preferably administered as a pharmaceutical composition. Accordingly, the disclosure provides pharmaceutical compositions comprising a compound or pharmaceutically acceptable salt of any of the active compounds described herein, together with at least one pharmaceutically acceptable carrier. The pharmaceutical composition/combination may contain a compound or salt of any of the active compounds described herein as the only active agent, but in another embodiment may also contain at least one additional active agent. In certain embodiments it is preferred that the additional active agent is an NS3 protease inhibitor or NS5A or NS5B inhibitor. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. In certain embodiments the active compound is delivered in an oral dosage form such as a pill, tablet or capsule in an effective amount, which may in some embodiments be at least 10, 25, 50, 100, 150, 200, 250, 300, 350 or 400 mg. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1, and the other active agent may be, for example, an NS3 protease inhibitor, an NS5A inhibitor or another NS5B inhibitor.

Compounds disclosed herein may be administered by any suitable means, including orally, topically, parenterally, by inhalation or spray, sublingually, transdermally, via buccal or transmucosal administration, rectally, as an ophthalmic solution, injection, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and should be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present disclosure.

The pharmaceutical compositions/combinations can be formulated for oral administration. These compositions contain between 0.1 and 99 weight % (wt. %) of a compound of Formula I and usually at least about 5 wt. % of a compound of formula. Some embodiments contain from about 25 wt. % to about 50 wt. % or from about 5 wt. % to about 75 wt. % of the compound of formula.

An effective amount of a pharmaceutical composition/combination of the disclosure may be an amount sufficient, for example, to (a) inhibit the progression of hepatitis C; (b) cause a regression of the hepatitis C infection; (c) cause a cure of a hepatitis C infection such that HCV virus or HCV antibodies can no longer be detected in a previously infected patient's blood or plasma, or (d) treat an HCV-associated disorder. An amount of a pharmaceutical composition/combination effective to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood can be markers of a halt in progression or regression of hepatitis C infection. Other hepatitis C disease markers include aminotransferase levels, particularly levels of the liver enzymes AST and ALT. These levels will typically be elevated in a HCV infected patient. Disease regression is usually marked by the return of AST and ALT levels to the normal range.

The compound or pharmaceutically acceptable salt of Formula I and at least one additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the disclosure may comprise administering or delivering the compound or salt of any of the active compounds described herein, and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

The pharmaceutical packaging may include an active compound or salt as described herein in a container together with instructions for using the compound to treat a patient suffering from Hepatitis C infection are included herein.

Packaged pharmaceutical compositions/combinations are also included herein. Such packaged combinations include any of the active compounds described herein in a container together with instructions for using the combination to treat or prevent a viral infection, such as a hepatitis C infection, in a patient.

The packaged pharmaceutical composition/combination may include one or more additional active agents. In certain embodiments the additional active agent is an NS3 protease inhibitor, an NS5A or another NS5B inhibitor.

The packaged pharmaceutical combination may include an active compound described herein or pharmaceutically acceptable salt of an active compound described herein and the additional active agent provided simultaneously in a single dosage form, concomitantly in separate dosage forms, or provided in separate dosage forms for administration separated by some amount of time that is within the time in which both the active compound described herein and the additional active agent are within the bloodstream of the patient.

The packaged pharmaceutical combination may include an active compound described herein or pharmaceutically acceptable salt of an active compound described herein provided in a container with an additional active agent provided in the same or separate container, with instructions for using the combination to treat an HCV infection in a patient.

Abbreviations

The following abbreviations are used in the chemical process and the examples.

Ac$_2$O Acetic anhydride
AcOD Acetic Acid, deuterated
Aq. aqueous
BuOH Butanol
DCM Dichloromethane
EtOAc Ethyl Acetate
IBX 2-Iodoxybenzoic acid
MeOH Methanol
MTBE Methyl tert-butyl ether
PBS Phosphate Buffered Saline
PDC Pyridinium Dichromate
TEA Triethylamine
THF Tetrahydrofuran
$^t$BuMgCl tert-Butyl Magnesium Chloride Preparation of Highly Active Nucleoside Derivatives Processes are provided for the preparation of the active compounds disclosed herein. As an example, the compound of Formula II can be prepared by the steps

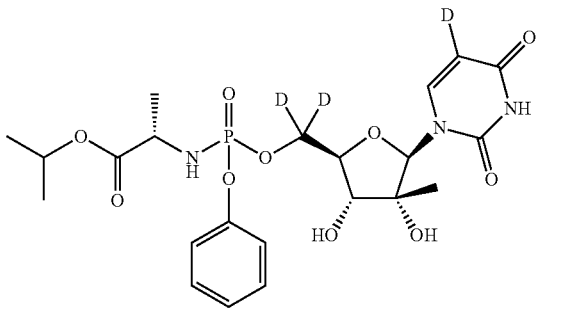 [SMILES: [2H]c1cn([C@@H]2O[C@H](C([2H])([2H])OP(=O)(N[C@@H](C)C(=O)OC(C)C)Oc3ccccc3)[C@@H](O)[C@@]2(C)O)c(=O)[nH]c1=O]

comprising:
(i) reacting an amino ester (100), wherein the amino ester is L-alanine isopropyl ester, with a dichlorophosphate (200), wherein the dichlorophosphate is phenoxydichlorophosphate, to form a reaction mixture;

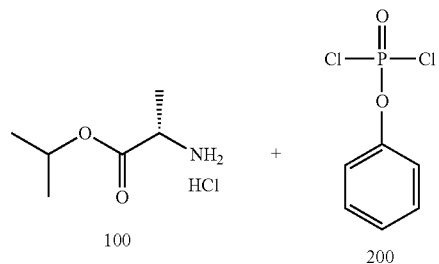

(ii) adding to the reaction mixture of (i) an aryl hydroxyl or aryl sulfhydryl, R-LH where L is S or O, and R is an optionally substituted aryl, heteroaryl, or heterocycloalkyl group such as phenyl, pyrrole, pyridyl, pyridinyl, or indole, or alternatively R-LH can be an N-hydroxyimide such as N-hydroxysuccinimide or N-hydroxyphthalimide, and in certain embodiments R-LH is

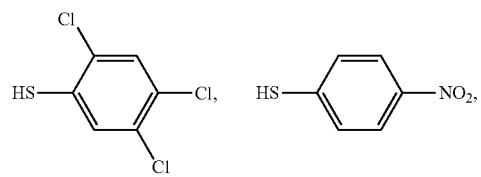

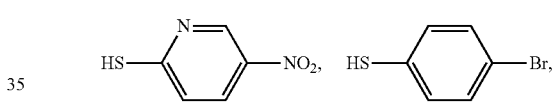

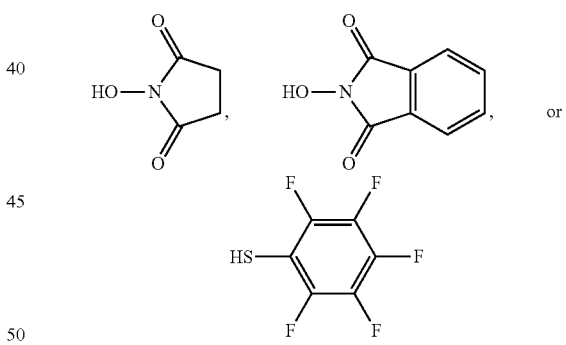

to form an intermediate (300)

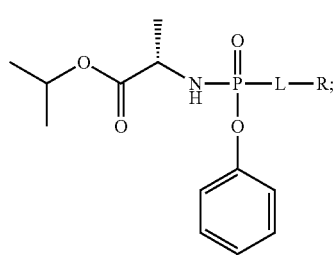

and (iii) reacting the intermediate (300) with a nucleoside (400)

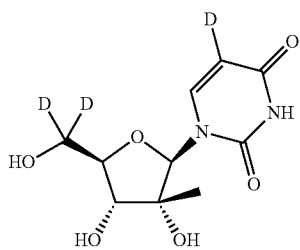

to form

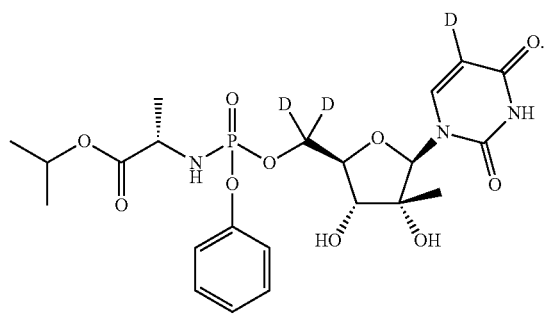 [SMILES: [2H]c1cn([C@@H]2O[C@H](C([2H])([2H])OP(=O)(N[C@@H](C)C(=O)OC(C)C)Oc3ccccc3)[C@@H](O)[C@@]2(C)O)c(=O)[nH]c1=O]

In certain embodiments the intermediate (300) has the following stereochemistry

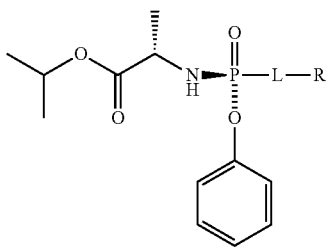

and a product of Formula IIA is produced.

(Formula IIA)

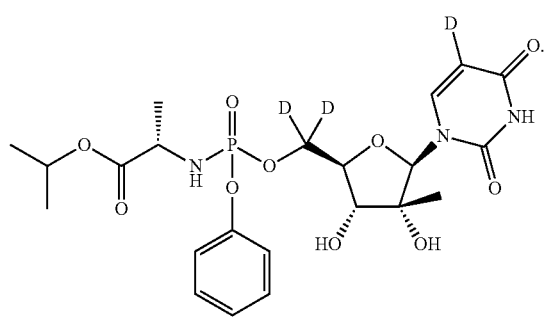

In certain embodiments the amino ester (100) and the dichlorophosphate (200) are combined at a temperature less than −20° C., more preferably at a temperature of about −40° C. to about −60° C.

In certain embodiments triethylamine or other base is added to the mixture of amino ester (100) and the dichlorophosphate (200). In certain embodiments the addition occurs in an organic solvent, such as dichloromethane, or other organic solvent such as 2-methyltetrahydrofuran or tetrahydrofuran.

Aryl hydroxyl or aryl sulfhydryl is added to the reaction mixture formed by the combination of amino ester (100) and dichlorophosphate (200). In certain embodiments the aryl hydroxyl or aryl sulfhydryl is trichlorothiophenol, but may also be replaced by other groups such as nitrothiophenol, bromothiophenol, N-hyrdoxysuccinamide, N-hydroxypthalimide, nitrohydroxypyridine. In certain embodiments the aryl hydroxyl or aryl sulfhydryl is added as a solution in dichloromethane or other organic solvent such as 1-propanol, 2-methyltetrahydrofuran, or tetrahydrofuran. In certain embodiments the solution containing the aryl hydroxyl or aryl sulfhydryl also contains triethylamine or other base. After the aryl hydroxyl or aryl sulfhydryl is added to the reaction mixture formed by the combination of amino ester (100) and dichlorophosphate (200) the resulting solution can be warmed to a temperature above 0° C., above 15° C., and preferably to about 20° C. to about 35° C. and may be stirred at this temperature for a period of from about 5 hours to about 30 hours and more preferably from about 10 hours to about 20 hours or about 15 hours.

The reaction mixture formed by the addition of aryl hydroxyl or aryl sulfhydryl to amino ester (100) and dichlorophosphate (200) may be extracted with water, which is optionally saturated with salt such as sodium bicarbonate or ammonium sulfate. The crude intermediate (300) obtained by drying the organic fraction may be purified by column chromatography, recrystallization, or other suitable purification method. The desired isomer of the intermediate (300) may be obtained by dissolving the intermediate, preferably after purification, in ethyl acetate/heptane or other mixture of other non-polar/polar aprotic solvent such as a mixture of heptane, cyclohexane, benzene (non-polar solvents) and THF, DMF, or DCM (polar aprotic solvents) and seeding the solution with a small amount of the desired isomer of intermediate (300). (This seed amount of (300) may have been obtained by another method.)

The nucleoside (400) may be suspended in a solvent, preferably a nonpolar aprotic solvent such as THF, DCM, or DMF. The suspension of nucleoside (400) in solvent may cooled below 0° C., preferably below −10° C. to about −40° C., and preferably to about −20° C. Note that nucleoside 400 is labeled Formula VI or compound 9 elsewhere in the specification. For convenience, 100 thru 400 are used in this discussion of the synthetic method.

The suspension of nucleoside (400) in solvent may be added to a base such as a Grignard reagent, for example tert-butyl MgCl, or other alkylmetal halide, at a temperature below 0° C., preferably below −10° C. to about −40° C., and preferably to about −20° C. The reaction mixture of nucleoside (400) in solvent and base is warmed to above 0° C., and preferably to about 20° C. to about 30° C., and stirred for about 1 to about 5 hours, or for preferably from about 2 to about 3 hours. The reaction mixture may then be cooled again to below 0° C., preferably below −5° C. to about −20° C., and preferably to about −10° C. Intermediate (300), which may optionally be optically pure, is added to the reaction mixture containing the nucleoside (400). The reaction mixture of intermediate (300) and nucleoside (400) is warmed to above 0° C., and preferably to about 20° C. to about 30° C., and stirred for at least 5 hours, preferably about 10 to about 20 hours, or preferably about 15 hours. The reaction may be cooled to about 0° C. and quenched with ammonium chloride or an acid, such as HCl or other acid capable of providing a pH of approximately 1 to 3 or preferably about 2. The resulting product, a compound of Formula I, may then be purified by organic phase extraction, column chromatography, HPLC, crystallization or any other suitable purification method.

In addition to a method of making a compound of the present disclosure, the disclosure also provides intermediates (300) useful for making a compound of Formula I:

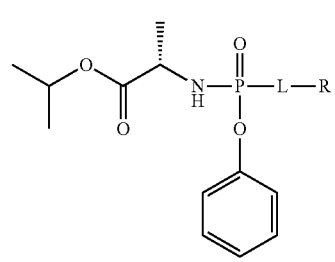

300 where -L-R is defined above.

In certain embodiments the intermediate is

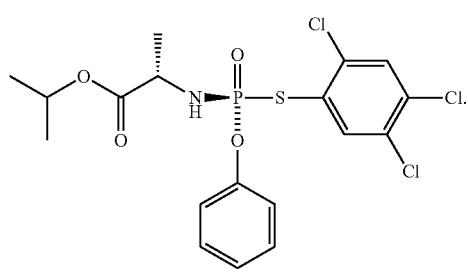 [SMILES: CC(C)OC(=O)[C@H](C)N[P@](=O)(Oc1ccccc1)Sc1cc(Cl)c(Cl)cc1Cl]

In other embodiments the intermediate is

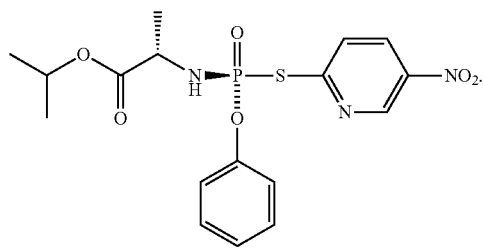 [SMILES: CC(C)OC(=O)[C@H](C)N[P@](=O)(Oc1ccccc1)Sc1ccc([N+](=O)[O-])cn1]

EXAMPLES

Example 1

(S)-isopropyl 2-(((S)-(perfluorophenoxy)(phenoxy)phosphoryl)amino)propanoate (Compound 1)

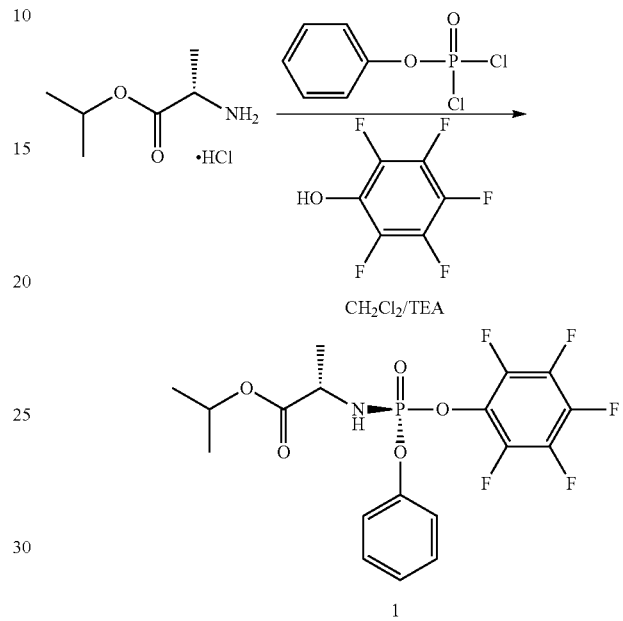

1

L-Alanine isopropyl ester HCl salt (160 g) is charged in a 5 L four-necked flask equipped with mechanical stirrer, thermometer and dropping funnel To the flask, dichloromethane (1 L) is added and the suspension is cooled to −70° C., followed by addition of triethylamine (200 g, 276 mL) over 45 min. To the mixture is added a solution of phenyl dichlorophosphate (200 g) in dichloromethane (1 L) over 2.5 h. The reaction mixture is stirred at this temperature for an additional 90 min and then allowed to warm up to 0° C. over a period of 2 h and stirred for 2 h at 0° C. To the mixture a solution of 2,3,4,5,6-pentafluorophenol (174.4 g) in 400 mL dichloromethane and a solution of triethylamine (105.4 g) in 200 mL dichloromethane are added dropwise simultaneously over a period of 1.2 h. The mixture is warmed to rt. and stirred overnight. The solid, triethylamine HCl salt, is filtered off and the cake is washed with dichloromethane (3×150 mL). The filtrate is concentrated under reduced pressure and the residue triturated with MTBE (3.0 L). The white solid is removed by filtration. The cake is washed with MTBE (3×150 mL). The filtrate is concentrated and the resulting crude solid triturated with 20% ethyl acetate in hexane (2.0 L). The solid is collected by filtration and washed with 10% NaHCO$_3$ until the aq. phase reached pH 7, the solid is then washed with water and dried in a vacuum oven (55° C.) for 28 h. The dried solid is mixed with 500 mL heptane-EtOAc (5:1) and stirred for 1 h. The solid is collected by filtration and washed with heptane-EtOAc (5:1, 2×80 mL) to afford a >99% single isomer. The solid is dried to give compound 1.

In an alternative work-up procedure, the reaction mixture is filtered and the DCM layer is washed with an aq. 0.1 N NaOH solution, followed by water, dried, and evaporated to dryness. The residue is suspended in heptane/EtOAc (5:1)

and the solid is filtered. The solid is resuspended in heptane/toluene (85:15) to isolate the pure single isomer.

Example 2

Preparation of (S)-isopropyl 2-(((R)-(((2S,3R,4R,5R)-5-(2,4-dioxo-3,4-dihydropyrimidin-1(2H)-yl)-3,4-dihydroxy-4-methyltetrahydrofuran-2-yl)dideuteromethoxy)(phenoxy)phosphoryl)amino)propanoate (Compound 7)

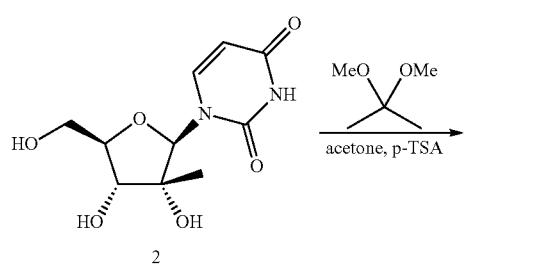

2

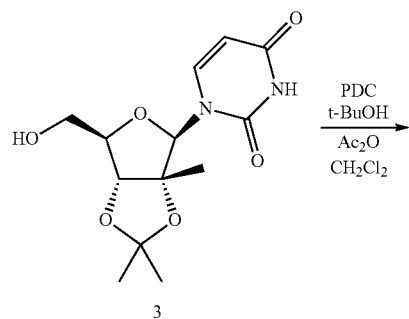

3

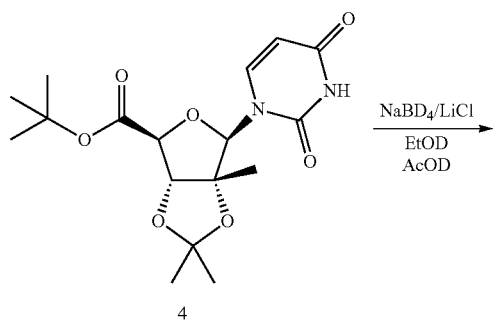

4

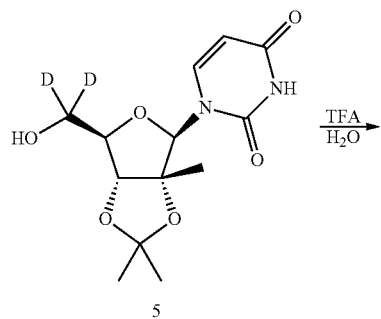

5

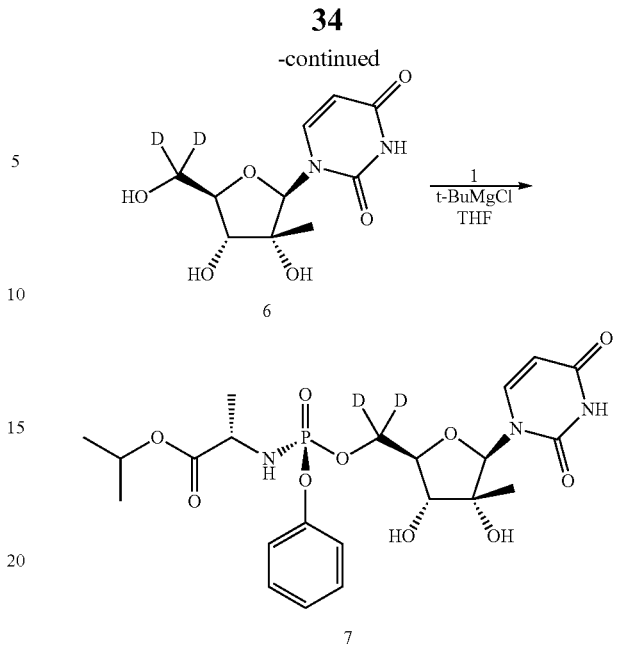

2,2-Dimethylpropane (140 mL) is added to 2'-C-methyluridine 2 (100 g) in acetone (700 mL). The resulting mixture is cooled in an ice bath for 30 min, then p-toluenesulfonic acid (11 g) is added and the reaction mixture is stirred at rt. for 24 h. After completion of the reaction (monitored by HPLC), the reaction mixture is cooled in an ice bath for 30 min and neutralized using cold potassium carbonate (12 g in 13 mL water, pH 7-8). The solvent is removed under reduced pressure until dryness. THF (~500 mL) is added to the residue and the solids are removed by filtration. The filtrate is co-evaporated with silica gel and purified by chromatography over silica gel (5-15% MeOH in $CHCl_3$) to give compound 3. $^1$H NMR (400 MHz, DMSO-$d_6$, 300 K): δ 1.22 (s, 3H), 1.34 (s, 3H), 1.49 (s, 3H), 3.63 (dd, J=12.0 Hz, 2.8 Hz, 1H), 3.69 (dd, J=12.0 Hz, 3.1 Hz, 1H), 4.15 (m, 1H), 4.47 (d, J=2.8 Hz, 1H), 5.25 (br s, 1H), 5.63 (dd, J=8.2 Hz, 2.3 Hz), 6.01 (s, 1H), 7.85 (d, J=8.2 Hz, 1H), 11.37 (s, 1H); LC-MS: 299 amu (M+1).

Compound 4 is prepared following the procedure reported by Corey et al. (*J. Org. Chem.* 1984, 49, 4735) with modifications described below. To acetonide 3 (50 g) in $CH_2Cl_2$ (1 L) is added PDC (126.1 g) at rt. followed by $Ac_2O$ (171 g) and t-BuOH (248 g). The reaction temperature is maintained below 35° C. during the addition of reagents and then stirred at rt. for 5 h. The reaction mixture is poured into aq. $K_2CO_3$ (250 g in 600 mL $H_2O$) and the organic layer is washed with $CuSO_4$ (100 g in 1 L $H_2O$). Activated charcoal (10 g) and silica gel (100 g) are added to the organic layer and stirred for 30 min and filtered. The filtrate is evaporated and residue purified by chromatography over silica gel (0-50% EtOAc in $CHCl_3$) to afford 4. $^1$H NMR (400 MHz, DMSO-$d_6$, 300 K): δ 1.25 (s, 3H), 1.41 (s, 3H), 1.46 (s, 9H), 1.48 (s, 3H), 3.31 (s, 1H), 4.61 (s, 1H), 4.79 (s, 1H), 5.70 (dd, J=8.1 Hz, 2.0 Hz, 1H), 5.93 (br s, 1H), 7.97 (d, J=8.1 Hz, 1H), 11.41 (s, 1H); LC-MS: 369 amu (M+1).

Lithium chloride (1.76 g) was stirred with $NaBD_4$ (1.58 g) in EtOD for 1 h. Compound 4 (2.97 g) was added to this solution and stirred at rt. for 3 h and quenched with acetic acid-d, diluted with ethyl acetate, washed with brine, and evaporated to dryness. The residue was purified by chromatography over silica gel to give the 5'-dideuterated compound 5.

Compound 5 (2.1 g) was treated with trifluoroacetic acid in the presence of water to give the 5'-dideuterated nucleoside 6. $^1$H NMR (400 MHz, CD$_3$OD, 300 K): δ 1.16 (s, 3H), 3.84 (d, J=9.2 Hz, 1H), 3.91 (d, J=9.2 Hz, 1H), 5.67 (d, J=8.1 Hz, 1H), 5.96 (s, 1H), 8.14 (d, J=8.1 Hz, 1H); $^{13}$C NMR (100 MHz, CD$_3$OD, 300 K): δ 20.2, 73.4, 80.0, 83.8, 93.2, 102.3, 142.5, 152.5, 166.0 (ribose C-5' not observed).

Compound 6 (1.0 g) was converted to the phosphoramidate derivative 7 following the procedure described by Ross et al. (*J. Org. Chem.* 2011, 76, 8311). $^1$H NMR (400 MHz, CD$_3$OD, 300 K): δ 1.15 (s, 3H), 1.21 (2×d, J=6.3 Hz, 6H), 1.35 (dd, J=7.2 Hz, J$_{H,P}$=0.9 Hz, 3H), 3.79 (d, J=9.2 Hz, 1H), 3.91 (dq, JH,P=10.0 Hz, J=7.2 Hz, 1H), 4.08 (dd, J=9.2 Hz, J$_{H,P}$=2.2 Hz, 1H), 4.96 (septet, J=6.3 Hz, 1H), 5.60 (d, J=8.1 Hz, 1H), 5.96 (s, 1H), 7.20 (m, 1H), 7.26 (m, 2H), 7.37 (m, 2H), 7.67 (d, J=8.1 Hz, 1H); $^{31}$P NMR (162 MHz, CD$_3$OD, 300 K): δ 3.8; LC-MS: 530 amu (M+1).

Example 3

Preparation of (S)-isopropyl 2-(((S)-(((2R,3R,4R,5R)-5-(5-deutero-2,4-dioxo-3,4-dihydropyrimidin-1(2H)-yl)-3,4-dihydroxy-4-methyltetrahydrofuran-2-yl)dideuteromethoxy)(phenoxy)phosphoryl)amino)propanoate (Formula IIa, Compound 10)

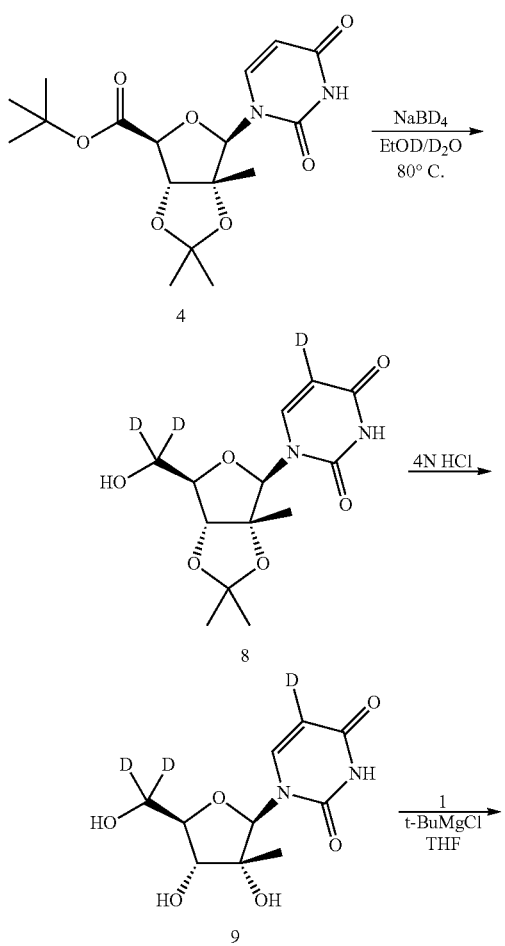

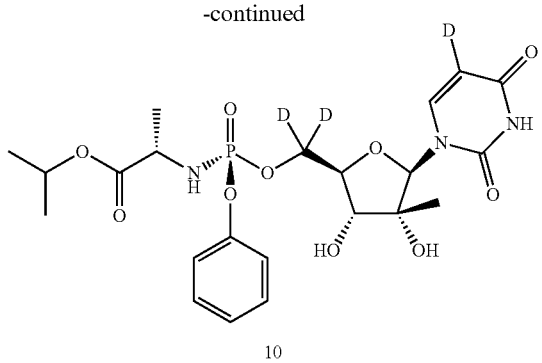

10

NaBD$_4$ (7.96 g) is added in portions to a cooled (5° C.) 70:30 v/v mixture of EtOD/D$_2$O (350 mL, 99% D) in a 1 L flask, followed by the addition of acetonide ester 4 (35 g) in portions (slowly bubbles). The resulting reaction mixture is stirred at rt. for 3 h, and then heated at 80° C. for 1 d ($^1$H NMR spectroscopic analysis indicates >85% deuterium incorporation at the 5-uracil position). The reaction mixture is filtered to remove solids and concentrated under reduced pressure to remove EtOD. Additional D$_2$O is added and the resulting mixture reheated at 95° C. to increase the deuterium incorporation at the 5 position to >98% (D-incorporation monitored by $^1$H NMR spectroscopy). After completion of the reaction, half the solvent is removed under reduced pressure, the mixture is cooled in an ice bath, AcOD (59 g) is added, and resulting mixture is stirred for 15-20 min. EtOAc (300 mL) and brine (100 mL) are added, the organic layer is separated, and the aq. layer is again extracted with EtOAc (150 mL), followed by THF (150 mL). The combined organic layers are concentrated, the resulting residue is dissolved in 10% MeOH and CHCl$_3$ (300 mL), filtered, concentrated, and purified by chromatography over silica gel (ISCO, eluent DCM/MeOH) to give the deuterated acetonide 8. $^1$H NMR (400 MHz, DMSO-d$_6$, 300 K): δ 1.22 (s, 3H), 1.36 (s, 3H), 1.49 (s, 3H), 3.31 (s, 2H), 4.14 (d, J=2.8 Hz, 1H), 4.47 (d, J=2.8 Hz, 1H), 5.21 (s, 1H), 6.01 (s, 1H), 7.85 (s, 1H), 11.36 (s, 1H); LC-MS: 302 amu (M+1).

Deuterated acetonide 8 (50 g) is added to a cooled (5° C.) 4 N HCl (250 mL) solution and stirred at rt for 3 h, during which time a white precipitate forms. The solvent is evaporated to dryness and to the residue is added water (100 mL) and stirred. The suspension is cooled to 5° C., stirred for 1 h. and the white precipitate is collected by filtration. The solid is washed with cold water (75 mL) and dried to afford the deuterated nucleoside 9. $^1$H NMR (400 MHz, CD$_3$OD, 300 K): δ 1.15 (s, 3H), 3.84 (d, J=9.2 Hz, 1H), 3.91 (d, J=9.2 Hz, 1H), 5.96 (s, 1H), 8.14 (s, 1H); $^{13}$C NMR (100 MHz, CD$_3$OD, 300 K): δ 20.2, 73.4, 80.0, 83.8, 93.2, 142.4, 152.5, 166.0 (ribose C-5' and uracil C-5 not observed); LC-MS: 262 amu (M+1).

Nucleoside 9 (37.3 g) in THF (750 mL) is cooled to −5° C. t-BuMgCl (1 M in THF, 430 mL) is added and the mixture is stirred for 30 min at the same temperature. The reaction mixture is stirred for another 30 minutes at it, then cooled again to −5° C., and a solution of 1 (129.5 g) in THF (650 mL) is added slowly. The reaction mixture is stirred at rt. for 24 h., cooled to −5° C., and to it added cold 2 N HCl (200 mL), followed by stirring for 10 min, and the addition of a saturated aq. solution of NaHCO$_3$ (~250 mL, pH ~8) and solid NaCl (50 g). The resulting mixture is stirred for 1 h. and the organic layer is separated. The aq. layer is extracted with THF (2×150 mL). All organic layers are combined and evaporated to dryness. The residue is purified partially over a short silica gel (500 mL) column (10-20% MeOH in CHCl₃), then purified additionally by chromatography over silica gel (ISCO, 4×300 g cartridge, eluted with 0-10% MeOH in CH₂Cl₂) to afford the title compound 10. $^1$H NMR (400 MHz, CD₃OD, 300 K): δ 1.15 (s, 3H), 1.21 (2×d, J=6.3 Hz, 6H), 1.35 (dd, J=7.2 Hz, $J_{H,P}$=0.9 Hz, 3H), 3.79 (d, J=9.2 Hz, 1H), 3.91 (dq, $J_{H,P}$=10.0 Hz, J=7.2 Hz, 1H), 4.08 (dd, J=9.2 Hz, $J_{H,P}$=2.3 Hz, 1H), 4.96 (septet, J=6.3 Hz, 1H), 5.96 (s, 1H), 7.20 (m, 1H), 7.26 (m, 2H), 7.37 (m, 2H), 7.67 (s, 1H); $^{31}$P NMR (162 MHz, CD₃OD, 300 K): δ 3.8; LC-MS: 531 amu (M+1).

Example 4

Alternative Preparation of Formula IIa (Compound 10)

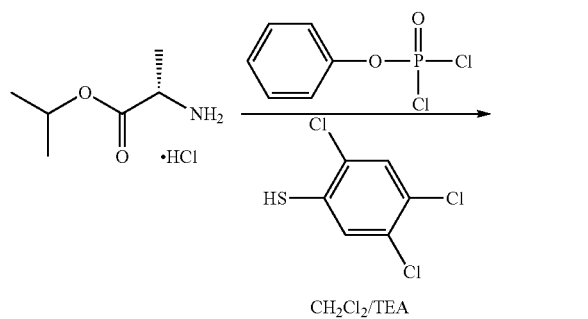

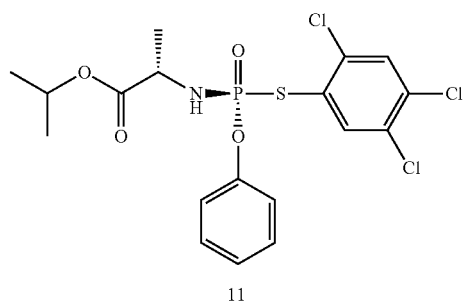

11

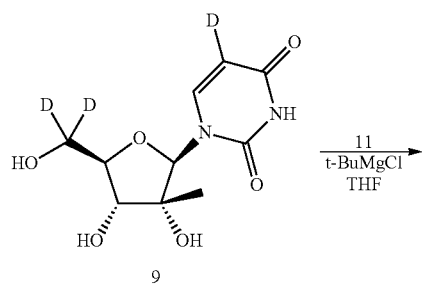

9

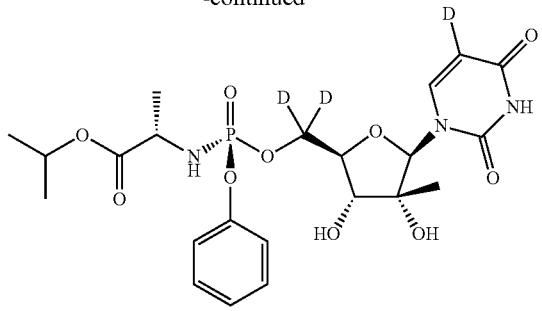

10

Phenoxydichlorophosphate (12.58 g) is added to a cold (−50° C.) solution of L-alanine isopropyl ester in CH₂Cl₂ (100 mL), followed by the addition of triethylamine (18.3 mL) in CH₂Cl₂ (36 mL) maintained at a temperature below −40° C. The reaction mixture is warmed to room temperature slowly and stirred for 2 h. and again cooled to −50° C. A solution of 2,4,5-trichlorothiophenol (12.74 g) in CH₂Cl₂ (20 mL) containing triethylamine (9.1 mL) is added. The reaction is warmed to rt. and stirred for 15 h. The reaction mixture is washed with water (~300 mL) followed by saturated aq. NaHCO₃ (~300 mL). The organic layer is separated, dried over Na₂SO₄, and evaporated to dryness under reduced pressure. The crude material is passed through a short column of silica (CH₂Cl₂/EtOAc 0:1 v/v to ~1:4 v/v) and the product is collected after evaporation of the solvent. The product is dissolved in 100 mL of 2.5% EtOAc in heptane and the solution seeded with compound 11 (~10 mg) and stirred for 1 h. at rt. The precipitate is collected by filtration, washed with a small amount of the above EtOAc/heptane solvent mixture, and dried to afford 11 as a single isomer. $^1$H NMR (400 MHz, CDCl₃, 300 K): δ 1.24 (d, J=6.3 Hz, 3H), 1.26 (d, J=6.3 Hz, 3H), 1.41 (d, J=7.0 Hz, 3H), 3.99-4.21 (m, 2H), 5.02 (septet, J=6.3 Hz, 1H), 7.17-7.24 (m, 3H), 7.34 (m, 2H), 7.52 (s, 1H), 7.73 (d, $J_{H,P}$=2.2 Hz, 1H); $^{31}$P NMR (162 MHz, CDCl₃, 300 K): δ 21.1.

A suspension of 9 (1.0 g) in THF is cooled to −20° C. and t-BuMgCl (11.6 mL, 1 M in THF) is added slowly, maintaining the temperature of the mixture below −20° C. The reaction mixture is warmed slowly to rt. (~2 h), stirred for 2 h, and then cooled to −10° C. Compound 11 (3.74 g) is added and the reaction mixture is warmed to rt. and stirred. After 15 h, the reaction mixture is cooled to 0° C., 2 N aq. HCl is added (to pH ~2), and the solution is stirred for 30 min at 0° C. Aqueous NaHCO₃ is added (to pH ~8), followed by NaCl (~3 g), and the mixture is stirred for 30 min. The organic layer is separated, dried, and evaporated under reduced pressure. The crude material is purified by column chromatography on silica gel (5% MeOH in CH₂Cl₂) to afford pure 10.

After compound 11 is isolated by filtration, the filtrate, which is enriched in the other stereoisomer at phosphorus, can be concentrated and purified by chromatographic techniques. This stereoisomer of 11 is treated with nucleoside 9 to give compound 31 described in Example 12.

Example 5

Alternative Preparation of Formula II (Compound 10)

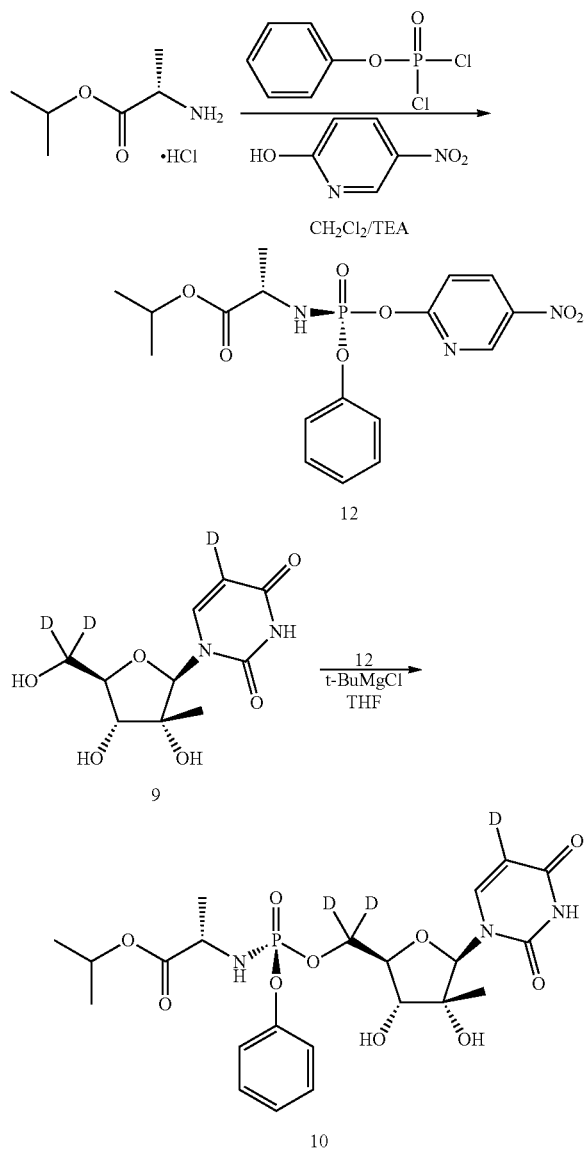

Compound 12 is prepared in a manner analogous to that described above in Example 4 for compound 11. Spectroscopic data for 12: $^1$H NMR (400 MHz, CDCl$_3$, 300 K): δ 1.19 (d, J=6.3 Hz, 3H), 1.22 (d, J=6.3 Hz, 3H), 1.39 (d, J=6.7 Hz, 3H), 4.25-4.38 (m, 2H), 4.96 (septet, J=6.3 Hz, 1H), 7.10 (d, J=9.0 Hz, 1H), 7.19 (m, 1H), 7.25 (m, 2H), 7.34 (m, 2H), 8.50 (dd, J=9.0 Hz, J=2.9 Hz, 1H), 9.15 (d, J=2.9 Hz, 1H); $^{31}$P NMR (162 MHz, CDCl$_3$, 300 K): δ −3.4.

Nucleoside 9 is treated with compound 12 in a manner analogous to that described in Example 3 to give compound 10.

Compound 31 described in Example 12 can be prepared using the other stereoisomer of compound 12 in a manner analogous to that described in Example 4.

Example 6

Preparation of (S)-isopropyl 2-(((S)-(((2R,3R,4R,5R)-5-(5-deutero-2,4-dioxo-3,4-dihydropyrimidin-1(2H)-yl)-3,4-dihydroxy-4-methyltetrahydrofuran-2-yomethoxy)(phenoxy)phosphoryl)amino)propanoate (Compound 17)

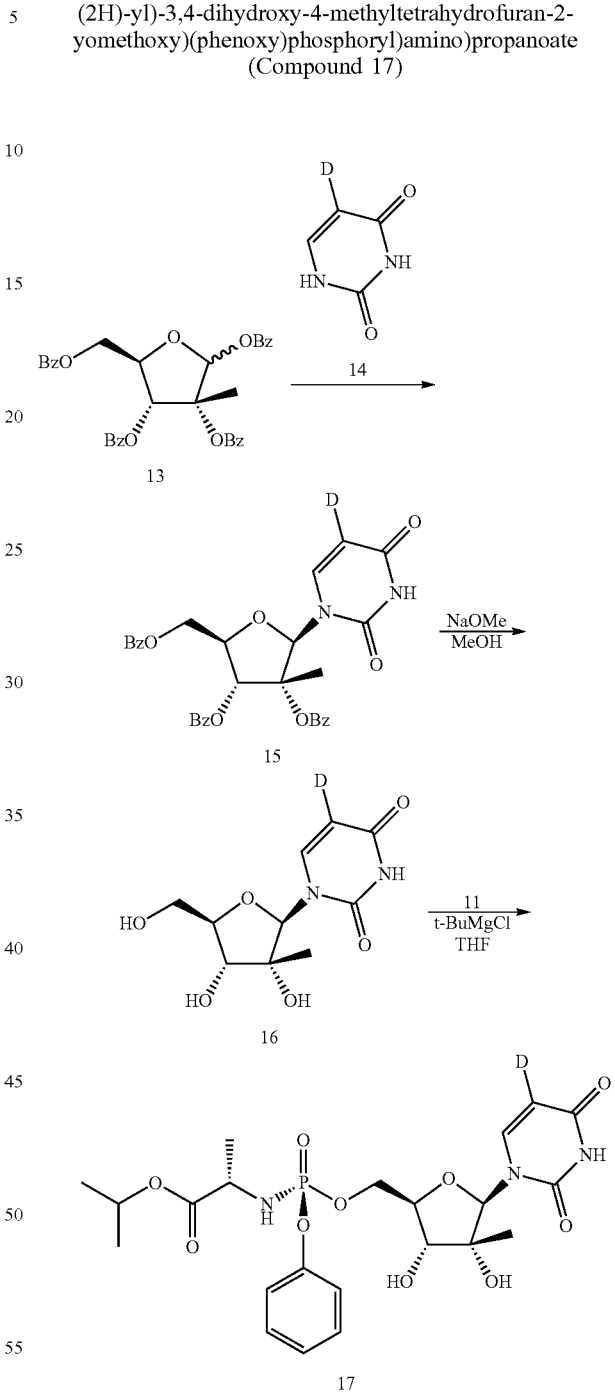

1,2,3,5-Tetra-O-benzoyl-2-C-methyl-β-D-ribofuranose 13 (2.44 g) was treated with uracil-5-d$_1$ 14 (1.0 g), following the procedure described in Harry-O'kuru et al. (*J. Org. Chem.* 1997, 62, 1754) using non-deuterated uracil, to give protected nucleoside 15. Compound 15 was treated with NaOMe in MeOH to give 2'-C-methyluridine-5-d$_1$ (16). $^1$H NMR (400 MHz, CD$_3$OD, 300 K): δ 1.16 (s, 3H), 3.78 (dd, J=12.5 Hz, 2.6 Hz, 1H), 3.84 (d, J=9.2 Hz, 1H), 3.92 (d of app t, J=9.2 Hz, 2.4 Hz, 1H), 3.98 (dd, J=12.5 Hz, 2.2 Hz, 1H), 5.96 (s, 1H), 8.14 (s, 1H); $^{13}$C NMR (100 MHz, CD$_3$OD, 300 K): δ 20.2, 60.5, 73.4, 80.0, 83.9, 93.1, 142.4, 152.5, 166.0 (uracil C-5 not observed).

Compound 16 (0.7 g) was converted to the phosphoramidate derivative 17 in a manner analogous to that described in Example 3. $^1$H NMR (400 MHz, CD$_3$OD, 300 K): δ 1.15 (s, 3H), 1.21 (2×d, J=6.3 Hz, 6H), 1.35 (dd, J=7.2 Hz, $J_{H,P}$=0.9 Hz, 3H), 3.79 (d, J=9.2 Hz, 1H), 3.91 (dq, $J_{H,P}$=10.0 Hz, J=7.2 Hz, 1H), 4.08 (m, 1H), 4.37 (ddd, J=11.8 Hz, $J_{H,P}$=5.9 Hz, J=3.7 Hz, 1H), 4.50 (ddd, J=11.8 Hz, $J_{H,P}$=5.9 Hz, J=2.0 Hz, 1H), 4.96 (septet, J=6.3 Hz, 1H), 5.96 (s, 1H), 7.20 (m, 1H), 7.26 (m, 2H), 7.37 (m, 2H), 7.67 (s, 1H); $^{31}$P NMR (162 MHz, CD$_3$OD, 300 K): δ 3.8; LC-MS: 529 amu (M+1).

Example 7

Preparation of (S)-isopropyl 2-(((S)-(((2R,3R,4R,5R)-5-(6-deutero-2,4-dioxo-3,4-dihydropyrimidin-1(2H)-yl)-3,4-dihydroxy-4-methyltetrahydrofuran-2-yl)methoxy)(phenoxy)phosphoryl)amino)propanoate (Compound 18)

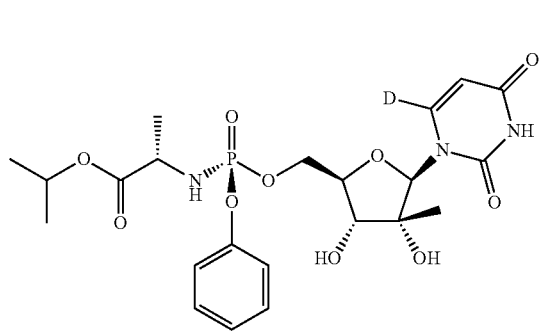

18

Compound 18 was prepared using uracil-6-d$_1$ in a manner analogous to that described for compound 17 in Example 6. $^1$H NMR (400 MHz, CD$_3$OD, 300 K): δ 1.15 (s, 3H), 1.21 (2×d, J=6.3 Hz, 6H), 1.35 (dd, J=7.2 Hz, $J_{H,P}$=0.9 Hz, 3H), 3.79 (d, J=9.2 Hz, 1H), 3.91 (dq, $J_{H,P}$=10.0 Hz, J=7.1 Hz, 1H), 4.09 (m, 1H), 4.37 (ddd, J=11.8 Hz, $J_{H,P}$=5.9 Hz, J=3.7 Hz, 1H), 4.50 (ddd, J=11.8 Hz, $J_{H,P}$=5.9 Hz, J=2.0 Hz, 1H), 4.96 (septet, J=6.3 Hz, 1H), 5.60 (s, 1H), 5.96 (s, 1H), 7.20 (m, 1H), 7.26 (m, 2H), 7.37 (m, 2H); $^{31}$P NMR (162 MHz, CD$_3$OD, 300 K): δ 3.8; LC-MS: 529 amu (M+1).

Example 8

Preparation of (S)-isopropyl 2-(((S)-(((2R,3R,4R,5R)-5-(5,6-dideutero-2,4-dioxo-3,4-dihydropyrimidin-1(2H)-yl)-3,4-dihydroxy-4-methyltetrahydrofuran-2-yl)methoxy)(phenoxy)phosphoryl)amino)propanoate (Compound 19)

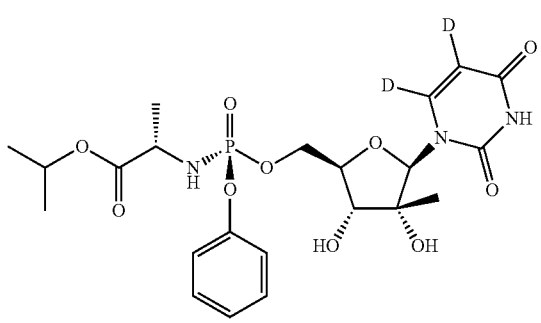

19

Compound 19 was prepared using uracil-5,6-d$_2$ in a manner analogous to that described for compound 17 in Example 6. $^1$H NMR (400 MHz, CD$_3$OD, 300 K): δ 1.15 (s, 3H), 1.21 (2×d, J=6.3 Hz, 6H), 1.35 (dd, J=7.2 Hz, $J_{H,P}$=0.9 Hz, 3H), 3.79 (d, J=9.2 Hz, 1H), 3.91 (dq, $J_{H,P}$=10.0 Hz, J=7.2 Hz, 1H), 4.09 (m, 1H), 4.37 (ddd, J=11.8 Hz, $J_{H,P}$=5.9 Hz, J=3.7 Hz, 1H), 4.50 (ddd, J=11.8 Hz, $J_{H,P}$=5.9 Hz, J=2.0 Hz, 1H), 4.96 (septet, J=6.3 Hz, 1H), 5.96 (s, 1H), 7.20 (m, 1H), 7.26 (m, 2H), 7.37 (m, 2H); $^{31}$P NMR (162 MHz, CD$_3$OD, 300 K): δ 3.8; LC-MS: 530 amu (M+1).

Example 9

Preparation of (S)-isopropyl 2-(((S)-(((2R,3R,4R,5R)-5-(5,6-dideutero-2,4-dioxo-3,4-dihydropyrimidin-1(2H)-yl)-3,4-dihydroxy-4-methyltetrahydrofuran-2-yl)dideuteromethoxy)(phenoxy)phosphoryl)amino)propanoate (Formula I, Compound 22)

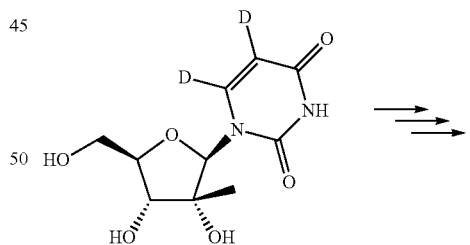

20

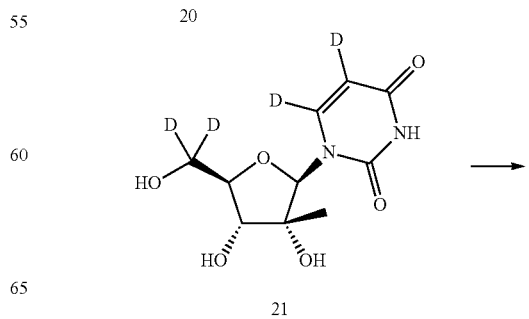

21

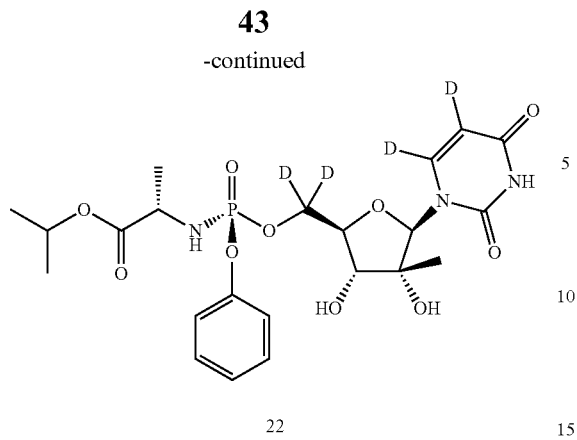

22

Nucleoside 20 was prepared via uracil-5,6-d$_2$ in a manner analogous to that described for compound 16 in Example 6. Nucleoside 20 was converted to deuterated nucleoside 21 in a manner analogous to that described for compound 8 in Examples 2 and 3. Spectroscopic data for 21: $^1$H NMR (400 MHz, CD$_3$OD, 300 K): δ 1.15 (s, 3H), 3.84 (d, J=9.2 Hz, 1H), 3.91 (d, J=9.2 Hz, 1H), 5.95 (s, 1H); $^{13}$C NMR (100 MHz, CD$_3$OD, 300 K): δ 20.2, 73.4, 80.0, 83.8, 93.1, 152.5, 166.0 (ribose C-5', uracil C-5, and uracil C-6 not observed). Nucleoside 21 was converted to the phosphoramidate derivative 22 in a manner analogous to that described in Example 3. Spectroscopic data for 22: $^1$H NMR (400 MHz, CD$_3$OD, 300 K): δ 1.15 (s, 3H), 1.21 (2×d, J=6.3 Hz, 6H), 1.35 (dd, J=7.2 Hz, J$_{H,P}$=0.9 Hz, 3H), 3.79 (d, J=9.2 Hz, 1H), 3.91 (dq, J$_{H,P}$=10.0 Hz, J=7.2 Hz, 1H), 4.08 (dd, J=9.2 Hz, J$_{H,P}$=2.2 Hz, 1H), 4.96 (septet, J=6.3 Hz, 1H), 5.95 (s, 1H), 7.20 (m, 1H), 7.26 (m, 2H), 7.37 (m, 2H); $^{31}$P NMR (162 MHz, CD$_3$OD, 300 K): δ 3.8; LC-MS: 532 amu (M+1).

Example 10

Preparation of (S)-isopropyl 2-(((S)-(((2R,3R,4R,5R)-5-(2,4-dioxo-3,4-dihydropyrimidin-1(2H)-yl)-3,4-dihydroxy-4-methyltetrahydrofuran-2-yl)deuteromethoxy)(phenoxy)phosphoryl)amino)propanoate (Formula III, Compound 26)

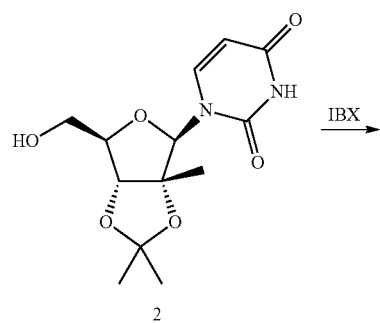

2

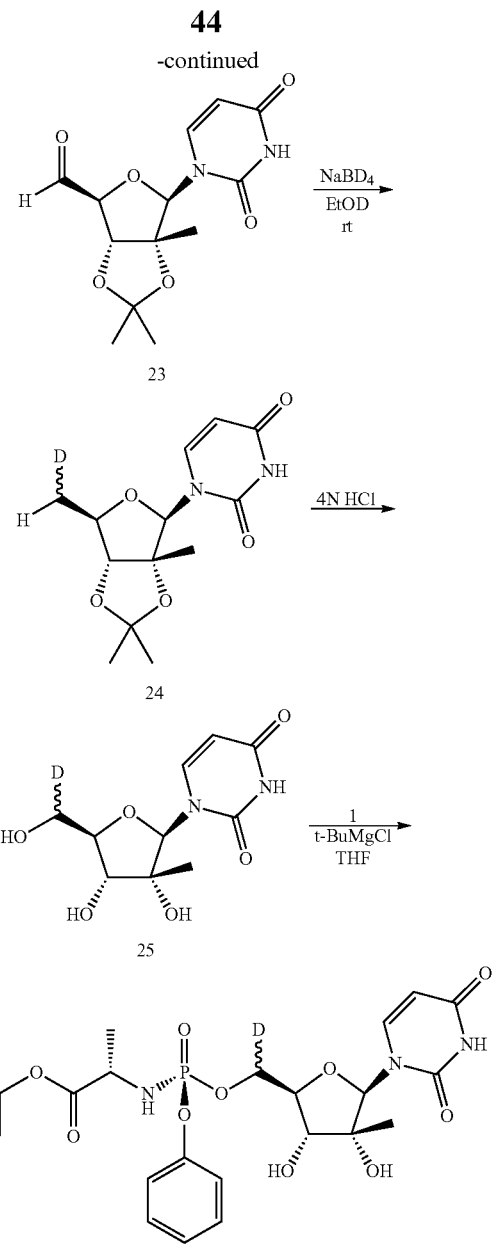

Commercially available 2-iodoxybenzoic acid (IBX, 3.54 g) is washed consecutively with acetonitrile (2×30 mL), acetone (2×20 mL), and Et$_2$O (10 mL), and then dried thoroughly in vacuo before use. A mixture of 2 (0.894 g) and washed IBX (2.52 g) in anhydrous acetonitrile (90 mL) is refluxed for 2 h. The mixture is cooled and filtered to remove solids. The filtrate is concentrated and treated with CH$_2$Cl$_2$. Solids are removed again by filtration and the filtrate is concentrated under reduced pressure to give 23 as a colorless foam.

Compound 23 (1.19 g) is dissolved in EtOD (15 mL), and into this turbid solution is added NaBD$_4$ (0.168 g) in portions at 0° C. with stirring. The reaction mixture is stirred at rt. for 2 h. and then cooled to 0° C. before adding a saturated aq. solution of NH$_4$Cl (1 mL) to quench the reaction. Brine (30 mL) is added and the mixture is extracted with EtOAc (5×30 mL). The combined organic extracts are died over anhydrous Na$_2$SO4, filtered, evaporated to dryness under reduced pressure. The crude material is purified by column chromatography on silica gel (10% MeOH in CH$_2$Cl$_2$ as eluent) to give 24.

Compound 25 is prepared in a manner analogous to that described for compound 8 in Examples 2 and 3. $^1$H NMR (400 MHz, CD$_3$OD, 300 K): δ 1.16 (s, 6H), 3.76 (br d, 2.6 Hz, 1H), 3.84 (d, J=9.2 Hz, 2H), 3.92 (d of d, J=9.2 Hz, 2.4 Hz, 2H), 3.96 (br d, J=2.2 Hz, 1H), 5.67 (d, J=8.1 Hz, 2H), 5.96 (s, 2H), 8.14 (2×d, J=8.1 Hz, 2H); $^{13}$C NMR (100 MHz, CD$_3$OD, 300 K): δ 20.2, 60.2 (t, J$_{H,D}$=21.3 Hz), 73.4, 80.0, 83.8, 93.1, 102.3, 142.5, 152.5, 166.0.

Phosphoramidate 26 is prepared in a manner analogous to that described for compound 10 in Example 3.

Example 11

Preparation of (S)-isopropyl 2-(((S)-(((2R,3R,4R,5R)-5-(5-deutero-2,4-dioxo-3,4-dihydropyrimidin-1(2H)-yl)-3,4-dihydroxy-4-methyltetrahydrofuran-2-yl)deuteromethoxy)(phenoxy)phosphoryl)amino)propanoate (Formula III, Compound 29)

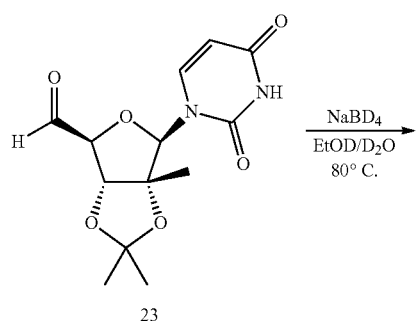

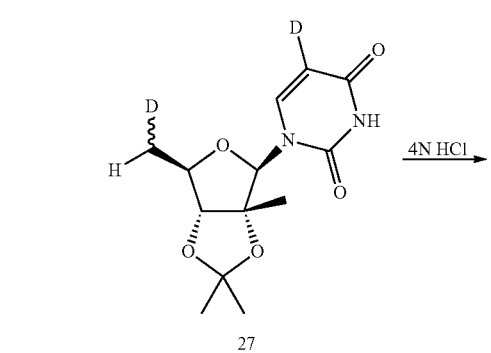

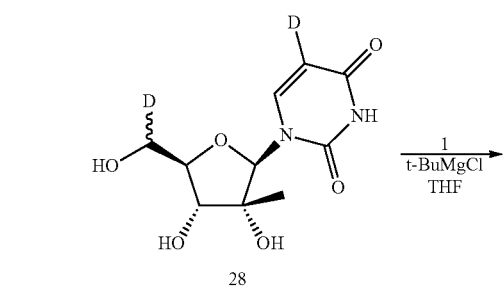

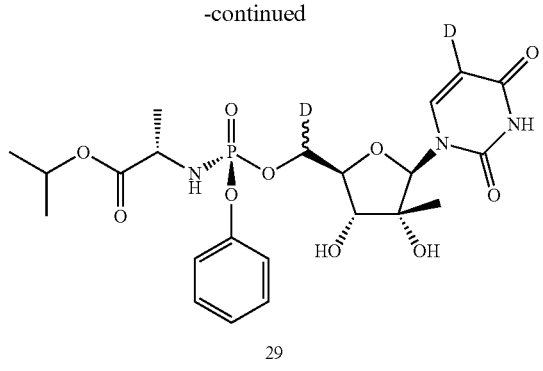

Compounds 27, 28, and 29 are prepared using methods analogous to those described in Example 3. Spectroscopic data for 29: $^1$H NMR (400 MHz, CD$_3$OD, 300 K): δ 1.16 (s, 6H), 3.76 (br d, 2.6 Hz, 1H), 3.84 (d, J=9.2 Hz, 2H), 3.92 (d of d, J=9.2 Hz, 2.4 Hz, 2H), 3.96 (br d, J=2.2 Hz, 1H), 5.96 (s, 2H), 8.14 (2×s, 2H); $^{13}$C NMR (100 MHz, CD$_3$OD, 300 K): δ 20.2, 60.2 (t, J$_{H,D}$=21.4 Hz), 73.4, 80.0, 83.8, 93.1, 142.4, 152.5, 166.0 (uracil C-5 not observed).

Example 12

Preparation of (S)-isopropyl 2-(((S)-(((2R,3R,4R,5R)-5-(5-deutero-2,4-dioxo-3,4-dihydropyrimidin-1(2H)-yl)-3,4-dihydroxy-4-methyltetrahydrofuran-2-yl)dideuteromethoxy)(phenoxy)phosphoryl)amino)propanoate (Compound 31)

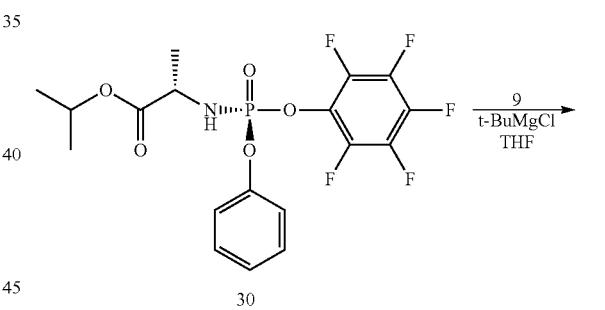

The combined MTBE and EtOAc/hexanes washings from the synthesis of compound 1 in Example 1 are concentrated under reduce pressure to give a mixture of 30 and 1. Nucleoside 9 is treated with this mixture in a manner analogous to that described in Example 3 to give the phosphoramidate derivatives 31 and 10. Pure 31 is isolated by preparative HPLC. $^1$H NMR (400 MHz, CD$_3$OD, 300 K):

δ 1.15 (s, 3H), 1.24 (d, J=6.3 Hz, 3H), 1.25 (d, J=6.3 Hz, 3H), 1.34 (dd, J=7.2 Hz, $J_{H,P}$=1.0 Hz, 3H), 3.80 (d, J=9.2 Hz, 1H), 3.92 (dq, $J_{H,P}$=9.0 Hz, J=7.2 Hz, 1H), 4.12 (dd, J=9.2 Hz, $J_{H,P}$=2.7 Hz, 1H), 5.00 (septet, J=6.3 Hz, 1H), 5.99 (s, 1H), 7.22 (m, 1H), 7.26 (m, 2H), 7.39 (m, 2H), 7.72 (s, 1H); $^{31}$P NMR (162 MHz, CD$_3$OD, 300 K): δ 3.9; LC-MS: 531 amu (M+1).

Example 13

Determination of Nucleoside Concentrations in Human Hepatocytes

For ease of reference, the following Formulas are referred to in the this example:

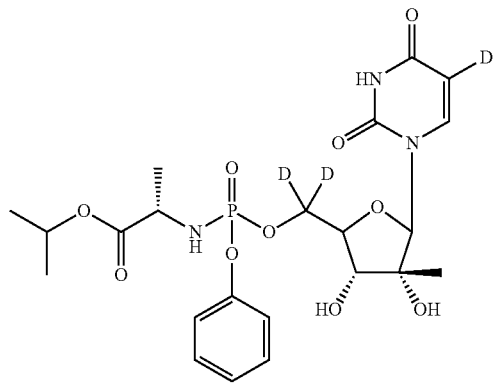

Formula II

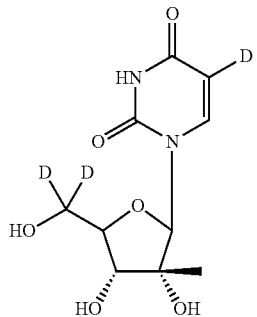

Formula VI

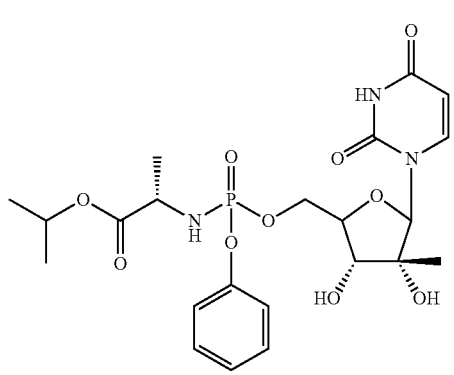

Formula VII

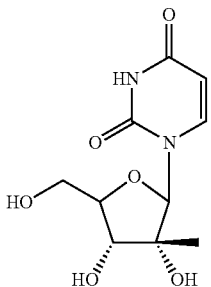

Formula IX

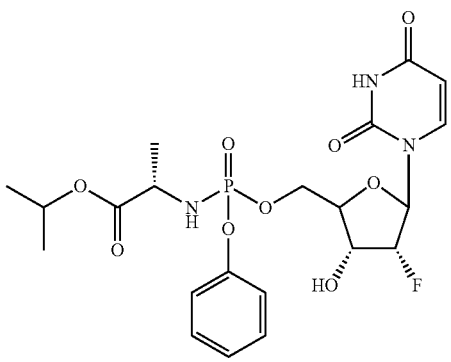

Formula X

Preparation of Hepatocyte Cells

Fresh liver hepatocytes were received plated in a 12-well or 6-well format (Life Technologies, Catalogue #HMFN12 and #HMNF06). Upon receipt, shipping media was removed immediately and replaced with 1 mL or 2 mL pre-warmed culture medium (Supplemented modified Chee's Media; Xenotech LLC, Catalogue #K2300) for 12- and 6-well formats, respectively. Cells were acclimated overnight at 37° C. with 5% CO$_2$ atmosphere. Media was aspirated from 12- and 6-well plates and replaced with 1 mL or 2 mL respectively of fresh media containing either 20 μM Formula II, 20 μM Formula VII, or solvent control (0.05% DMSO). Samples were incubated at 37° C., 5% CO$_2$ atmosphere, in duplicate for Formula II and in singlet for Formula VII in each well format. Stability of the compounds in the absence of cells was also assayed. At 24 hours, media was removed and frozen. Cells were washed twice with cold PBS. 70% cold Methanol (0.75 mL or 1.5 mL, for 12- and 6-well formats, respectively) containing Formula X as an internal standard was added to each well and cells were gently removed from the plate by scraping. The recovered cells suspended in the methanol solution were aspirated into a vial and frozen at −80° C.

Extraction and LC-MS/MS Analysis of Hepatocyte Cells

Cell solutions were extracted overnight at −80° C. in 70% methanol, removed from the freezer, defrosted and vortexed. Tubes were centrifuged at 3000 rpm for 15 minutes at 4° C. Supernatants were removed and analyzed by LC-MS/MS. Six concentrations of Formula II, Formula VII, Formula VI or Formula IX were prepared by 3-fold serial dilution in DMSO. Aliquots of the compounds at the specified concentrations were spiked into 70% methanol containing internal standard. Two concentrations were also spiked into cell solutions from the experiment incubated in the absence of compound. Samples were frozen at −80° C. overnight, then defrosted and vortexed. Samples were centrifuged at 3000 rpm for 15 minutes. Supernatants were removed and analyzed by LC-MS/MS. The calibration concentrations were 5, 1.67, 0.556, 0.185, 0.0617 and 0.0206 µM. The analytes were quantified using linear regression of calibration standard values with instrument response. The acceptance criteria used and calibration standard concentrations was ±30% of nominal concentration. Calibration standards that did not meet the specified criteria were not used in the calibration curve. Sample values were accepted when at least 66% of the standard concentrations during the run were within 30% of nominal. The "r" value required for acceptance of the run was >0.98. Cell samples were analyzed without internal standard due to only 81% extraction efficiency of internal standard from cells while calibration was conducted without cells, this gave more accurate determination of concentrations.

Extraction and LC-MS/MS Analysis of Hepatocyte Media

Hepatocyte media incubates were removed from the freezer, defrosted and vortexed. 2 parts hepatocyte media incubated to 1 part acetonitrile-containing internal standard were mixed and then centrifuged at 3000 rpm for 15 minutes at 4° C. Supernatants were removed and analyzed by LC-MS/MS. Controls were six concentrations of Formula II, Formula VII, Formula VI or Formula IX prepared by 3-fold serial dilution in DMSO. Aliquots of the compounds were spiked into fresh hepatocyte media to afford 5, 1.67, 0.556, 0.185, 0.0617 and 0.0206 µM concentrations of calibration media. 2 parts calibration media mixed with 1 part acetonitrile-containing internal standard samples were centrifuged at 3000 rpm for 15 minutes at 4° C. Supernatants were removed and analyzed by LC-MS/MS. Analyte concentrations in the samples were quantified using linear regression of calibration standard values with instrument response. The acceptance criteria used and calibration standard concentrations was ±30% of nominal concentration. Calibration standards that did not meet the specified criteria were not used in the calibration curve. Sample values were accepted when at least 66% of the standard concentrations during the run were within 30% of nominal. The "r" value required for acceptance of the run was >0.98.

As the data shows in Table 1 and Table 2 below, there is more dephosphorylated nucleoside (i.e., undesired 5'-OH nucleoside) in the samples incubated with the undeuterated phosphoramidate than with the 5'-deuterated phosphoramidate. Specifically, using 20 µM Formula II or its undeuterated Formula VII counterpart (12 well plate (1 ml) with hepatocytes seeded at 0.67 million cells per well for 24 hours) results in a 1.9 fold (media, i.e., extracellular concentration) and 2.9 fold (cell extract, i.e., intracellular) higher concentration of undeuterated dephosphorylated 2'-methyl uridine (Formula IX) compared to that resulting from the 5'-deuterated form (Formula VI). Results of incubation of 20 µM Formula II or its undeuterated counterpart (6 well plate (2 ml) with hepatocytes seeded at 1.7 million cells per well for 24 hours) indicate a 1.5 fold (cell extract, i.e., intracellular) and 2.8 fold (cell extract, i.e., intracellular) higher concentration in higher concentration of undeuterated dephosphorylated 2'-methyl uridine (Formula IV) compared to that resulting from the 5'-deuterated form (Formula VI). Thus, on average, the hepatocyte nucleotidase activity leads to about twice as much 5'-OH-nucleoside produced when the 5'-position is not deuterated. This difference in 5'-monophosphate pool available for activation to the triphosphate when 5'-deuterated nucleoside derivative is used can have a significant effect on efficacy, dosage, toxicity and/or pharmacokinetics of the drug.

Table 1 illustrates the concentration of Formula IX (the undeuterated 5'-OH 2'-methyluridine) and Formula VI (5'-deuterated-5'-OH 2'-methyluridine) in human hepatocyte media and cell extract after incubation with 20 µM of Formula VII or Formula II, respectively. Specifically, as described in Example 13, using 20 µM Formula II or its undeuterated Formula VII counterpart (12 well plate (1 ml) with hepatocytes seeded at 0.67 million cells per well for 24 hours) results in a 1.9 fold (media, i.e., extracellular concentration) and 2.9 fold (cell extract, i.e., intracellular) higher concentration of undeuterated dephosphorylated 2'-methyl uridine (Formula IX) compared to that resulting from the 5'-deuterated form (Formula VI).

TABLE 1

| | | Hepatocyte Media | | | Hepatocyte Cell Extract adjusted to volume of media | | |
| --- | --- | --- | --- | --- | --- | --- | --- |
| | | Buffer Stability | Nucleoside (Formula IX or Formula VI) | | | Nucleoside (Formula IX or Formula VI) | |
| Parent Compound | % Parent Remaining @ T24 hr | Parent T24 hr 37° C. | Conc (µM) | % 2 0 µM Dose | Parent Conc. (µM) | Conc (µM) | % 2 0 µM Dose |
| Formula VII | 0.82 | 97 | 8.4 | 42 | <0.02 | 0.044 | 0.22 |
| Formula II | 0.41 | 97 | 4.4 | 22 | <0.02 | 0.015 | 0.08 |

Table 2 illustrates the concentration of Formula IX (the undeuterated 5'-OH 2'-methyluridine) and Formula VI (5'-deuterated-5'-OH 2'-methyluridine) in human hepatocyte media and cell extract after incubation with 20 µM of Formula VII or Formula II, respectively. As described in Example 13, results of incubation of 20 µM Formula II or its undeuterated Formula VII counterpart (6 well plate (2 ml) with hepatocytes seeded at 1.7 million cells per well for 24 hours) indicate a 1.5 fold (cell extract, i.e., intracellular) and 2.8 fold (cell extract, i.e., intracellular) higher concentration of undeuterated dephosphorylated 2'-methyl uridine (Formula IX) compared to that resulting from the 5'-deuterated form (Formula VI).

TABLE 2

| | | Hepatocyte Media | | | Hepatocyte Cell Extract adjusted to volume of media | | |
| --- | --- | --- | --- | --- | --- | --- | --- |
| | | Buffer Stability | Nucleoside (Formula IX or Formula VI) | | | Nucleoside (Formula IX or Formula VI) | |
| Parent Compound | % Parent Remaining @ T24 hr | Parent T24 hr 37° C. | Conc (µM) | % 2 0 µM Dose | Parent Conc. (µM) | Conc (µM) | % 2 0 µM Dose |
| Formula VII | 4.9 | 97 | 5.2 | 26 | <0.02 | 0.057 | 0.28 |
| Formula II | 3.9 | 97 | 3.4 | 17 | <0.02 | 0.020 | 0.10 |

Example 14

Triphosphate Levels (Formula IV) in Comparison to Triphosphate Levels of VX-135-TP The results of three experiments comparing the triphosphate levels of Formula IV to the level of VX-135 triphosphate are described in this Example. Human hepatocytes were used according to the general methods described in Example 13. The concentrations of Formula IV produced in human liver hepatocytes (pmol Formula IV/million cells) were determined at 2, 4, 8, 25, or 48 hours of incubation with 5 µM Formula II.

As a comparison to a clinical trial candidate as further described in Example 14 and Table 3, a poster presented by Alios (EASL 2013) indicates that the level of VX-135 triphosphate measured in human hepatocytes after 24 hours incubation with 50 µM VX-135 was 1174 pmol/million cells. In contrast, the level of Formula IV after 25 hours of incubation of human hepatocytes with 5 µM of Formula II, i.e., a ten times lower concentration, is 486 pmol/million cells. Therefore, the amount of triphosphate produced by incubation of Formula II is 4-fold greater (does-normalized) than the amount of triphosphate produced by VX-135. While the precise structure of VX-135 is not currently known, it is a uridine nucleotide analog prodrug NS5B inhibitor.

Table 3 illustrates the concentrations of Formula IV (the active deuterated triphosphate metabolite of Formula II) produced in human liver hepatocytes (pmol Formula IV/million cells) at 2, 4, 8, 25, or 48 hours of incubation with 5 µM Formula II. The results of three experiments are shown, along with the mean and standard deviation determined for each time point. Peak levels of Formula IV were obtained at >48 hours in human hepatocytes. The concentration of VX-135-TP (the active triphosphate metabolite) generated from VX-135 is shown at 24 hours. As discussed in Example 14, the levels of triphosphate (Formula IV) generated from Formula II are 4-fold higher than levels of triphosphate (VX-135-TP) generated from VX-135, suggesting that VX-135 will be less potent than Formula II.

TABLE 3

| Time (hr) | Formula IV (pmol/million cells) | | | | VX-135-TP (pmol/million cells) |
| --- | --- | --- | --- | --- | --- |
| | rep 1 | rep 2 | rep 3 | Mean⁺StDev | |
| 2 | 72.1 | 71.5 | 67.9 | 70.5⁺2.25 | |
| 4 | 130 | 129 | 129 | 129⁺0.62 | |
| 8 | 218 | 217 | 236 | 224⁺10.6 | |
| 25 | 506 | 465 | 488 | 486⁺20.9 | 117.4 (Dose normalized) |
| 48 | 619 | 581 | 575 | 592⁺24.3 | |

Example 15

Determination of Formula IV Concentration from Formula II Dosing

The relationship of the concentration of Formula IV (ng/ml) as a result of Formula II (µM) concentration in human liver hepatocytes was determined. The general methods of Example 13 were used to determine compound concentrations. The Formula IV concentrations in human hepatocytes were determined after 24 hour incubations with 0.15, 0.45, and 1.35 µM Formula II. The results were plotted and the linear regression was calculated using Microsoft Excel. As shown in FIG. 1, there is a linear relationship at the concentrations tested for dosing of Formula II, and the resulting concentration of the active triphosphate compound (Formula IV).

Additionally, after incubation of Formula II at 50 nM in primary hepatocytes for 24 hours, the level of Formula IV ranged from 9.2-16.2 pmol/million cells. These concentrations are 5- to 8-fold higher than concentrations obtained when the Huh-luc/neo cells were incubated with 50 nM Formula II. Since Formula IV is the active species which inhibits HCV replicon replication in Huh-luc/neo cells, the predicted $EC_{50}$ of Formula II in primary human hepatocytes would be 6.25-10 nM (against a putative HCV in primary hepatocytes) presuming the linear relationship obtained in FIG. 1 between Formula II and Formula IV continues at lower concentration.

Example 16

Determination of the Half-Lives of Formula IV and GS-7977-TP

In this Example, the general methods of Example 13 were used to determine the half-lives of the active triphosphate (Formula IV or GS-7977-TP) in human, dog, monkey, and rat hepatocytes. Briefly, Formula II or GS-7977 (Sovaldi) were added at selected concentrations to hepatocytes (human, dog, monkey and rat) and incubated at 37° C. Supernatant cell extracts of Formula IV or GS-7977-TP (the active triphosphate metabolites) were measured by high performance liquid chromatography with tandem mass spectrometric detection (LC-MS/MS). Human hepatocyte cells used for half-life determinations were human liver hepatocyte 12-well format cells and were seeded at 0.67 million cells per well. Canine hepatocyte cells used for half-life determinations were beagle dog liver hepatocyte 12-well format cells and were seeded at 0.67 million cells per well. Monkey hepatocyte cells used for half-life determinations were Cynomolgus monkey liver hepatocyte 12-well format cells, and were seeded at 0.9 million cells per well. Rat hepatocyte cells for half-life determinations were Sprague-Dawley (SD) rat liver hepatocyte 12-well format cells, and were seeded at 0.67 million cells per well. All cells were obtained from Life Technologies.

As shown in Table 4, the half-life of Formula IV is greater than the half-life of the triphosphate of Sovaldi in hepatocytes from all four species. The longest half-life was in human hepatocytes, followed by dog, then monkey and then rat. The half-lives range from 10-30 hours for Formula IV and 8-23 hours for the triphosphate of Sovaldi.

Table 4 showing the half-lives of the active triphosphate (Formula IV or GS-7977-TP) in human, dog, monkey, and rat hepatocytes. Formula II or GS-7977 (Sovaldi) were added at selected concentrations to hepatocytes (human, dog, monkey and rat) and incubated at 37° C. Supernatant cell extracts of Formula IV or GS-7977-TP (the active triphosphate metabolites) were measured by high performance liquid chromatography with tandem mass spectrometric detection (LC-MS/MS). As discussed in Example 15, the triphosphate half-life values ranged from 8-30 hours and Formula IV generally had a longer half-life than GS-7977-TP across all species tested. (a—Values in parenthesis=95% confidence interval).

TABLE 4

| Species | Formula IV $t_{1/2}$ (hr) | GS-7977-TP $t_{1/2}$ (hr) |
| --- | --- | --- |
| Human | 27.6 (26.0-29.4)[a] | 22.6 (21.5-23.9) |
| Dog | 29.6 (22.0-45.4) | 17.7 (15.0-21.5) |
| Monkey | 14.5 (11.8-18.9) | 9.3 (7.9-11.4) |
| Rat | 10.2 (8.6-12.5) | 7.6 (6.4-9.3) |

Example 17

Triphosphate Levels (Formula IV and GS-7977-TP) in Human Hepatocytes

In this Example, the triphosphate levels of Formula IV and GS-7977-TP were determined using the general methods as described in Example 13. Results for the three experiments determining the triphosphate levels of Formula IV as described in the Table 3, are plotted graphically and shown in FIG. 2. Levels of the corresponding triphosphate of Sovaldi (GS-79777) were also determined for comparison and are shown in FIG. 3. Briefly, the concentrations of Formula IV or GS-7977-TP produced in human liver hepatocytes (pmol/million cells) were determined at 2, 4, 8, 25, or 48 hours of incubation with 5 µM Formula II or GS7977 (Sovaldi), respectively.

Figure 2:
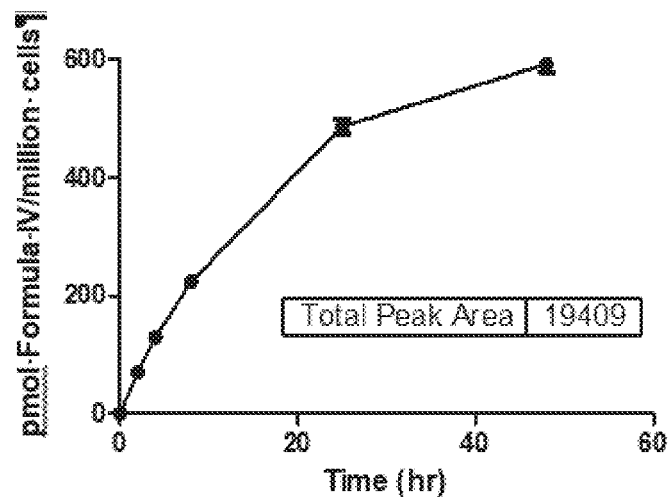
FIG. 2 is graph of the concentration of Formula IV (the active deuterated triphosphate metabolite of Formula II) produced in human liver hepatocytes (pmol Formula IV/million cells) during 48 hours of incubation with 5 µM Formula II. Concentrations were measured at the indicated times and the AUC was calculated with Graphpad Prism 5 software. As discussed in Example 16, peak levels of Formula IV were obtained at >48 hours in human hepatocytes.
Figure 3:
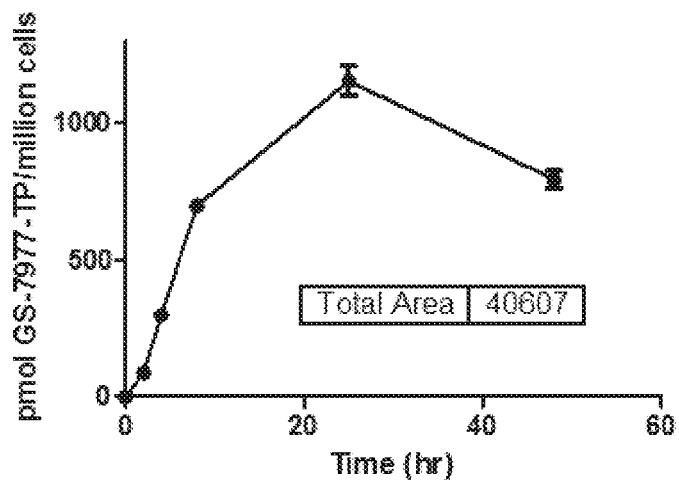
FIG. 3 is graph of the concentration of GS-7977-TP (the active triphosphate metabolite of Sovaldi) produced in human liver hepatocytes (pmol GS-7977-TP/million cells) during 48 hours of incubation with 5 µM GS-7977 (Sovaldi). Concentrations were measured at the indicated times and the AUC was calculated with Graphpad Prism 5 software. As discussed in Example 16, peak levels of GS-7977-TP (the active triphosphate metabolite of Sovaldi) were obtained at 24 hours in human hepatocytes.

Further, as described in Example 17 and FIGS. 2 and 3, over a 48 hour period, while the intracellular conversion to the corresponding triphosphate of Sovaldi (GS-7977) as measured in human hepatocytes is 2-fold greater than that of the triphosphate derived from Formula II (i.e., Formula IV), the concentration of Formula IV is still increasing at 48 hours, while the concentration of the triphosphate metabolite of Sovaldi decreases from 24 to 48 hours. The increasing concentration of Formula IV, combined with its half-life of >24 h, suggest accumulation of Formula IV (the triphosphate of Formula II) levels in hepatocytes on repeat dosing. This trend, after an initial in vivo initial dosing ramp up acclimation, can lead to a higher steady state concentration of Formula IV in vivo for the triphosphate derived from Formula II than the triphosphate of Sovaldi. In addition, the intrinsic potency (the inhibitory effect on the RdRp activity of NS5B) of Formula IV (the triphosphate of Formula II) is 1.5 fold better than the intrinsic potency of the triphosphate of Solvadi.

Example 18

NS5B RNA Polymerase IC$_{50}$ Determination

The NS5B RNA polymerase reaction was monitored via incorporation of [$\alpha$-$^{32}$P]-CTP into nascent RNA synthesized from a negative-strand RNA template derived from the HCV 5' nontranslated region (NTR) and including the internal ribosomal entry site (IRES).

To generate the negative-strand IRES RNA template, duplex DNA (NTR bases 1-341) was amplified from the HCV pFK-I$_{341}$PI-Luc/NS3-3'/ET plasmid using the primers 5'-NTR-1-21 (SEQ ID NO.:1) (GCCAGCCCCCT-GATGGGGGCGACACTCCAC) and T7-5NTR-341-317 (SEQ ID NO.:2) (GAAAT TAATACGACTCACTATAGGGGGTGCACGGTCTACG AGACCTCC, T7 promoter sequence underlined). Negative-strand RNA was transcribed from this duplex DNA using T7 RNA polymerase (MEGAscript T7 Transcription Kit, Life Technologies). RNA was purified from reaction components (MEGAclear, Life Technologies) and its yield and purity assessed by agarose gel electrophoresis and optical absorption.

NS5B RNA polymerase reactions for IC$_{50}$ determination were performed in 96-well microtiter plates in 20 µL reactions containing assay buffer (50 mM Na$^+$ HEPES, 1 mM MgCl$_2$, 0.75 mM MnCl$_2$, 2 mM DTT, pH 7.5), 1 U/µL SUPERase•In (Life Technologies), 20 ng/µL IRES RNA template, 1 µM each ATP, CTP, GTP, and UTP (Life Technologies) including [$\alpha$-$^{32}$P]-CTP at a final specific activity of 50 Ci/mmol (PerkinElmer), test compounds in 10-point half-log dilution series, and NS5B polymerase. Reactions were incubated at 27° C. for 60 minutes and terminated by dilution to 100 µL in 1× stop solution (final concentrations 144 mM Na$^+$ citrate, 1.44 M NaCl, 10 mM EDTA, pH 7.0). 80 µL stopped samples were applied by vacuum to nylon membrane filtermats (PerkinElmer), washed 4× in 60 mM Na$^+$ citrate, 600 mM NaCl (pH 7.0), rinsed sequentially in H$_2$O and EtOH, dried, and counted in a MicroBeta2 counter with scintillation cassette (PerkinElmer). NS5B polymerase activity was shown in parallel reactions to be within linear range. Compound activity was expressed as the concentration that reduced radiolabel incorporation by 50% (IC$_{50}$) as determined by sigmoidal curve-fitting using non-linear regression analysis (Prism Software, GraphPad, La Jolla, Calif.).

The inhibitory activity of nucleoside triphosphate compounds (Formula IV and GS-7977-triphosphate) against wild-type NS5B polymerase are shown in Table 5. The IC$_{50}$ values are presents as mean±standard deviation from N independent experiments for compounds against wild-type (WT) NS5B polymerase.

TABLE 5

|  | GT-1b WT[a] | |
|---|---|---|
| Compound | IC$_{50}$ (µM) | N |
| Formula IV | 1.4 ± 0.1 | 4 |
| GS-7977-TP | 2.1 ± 0.3 | 4 |

This specification has been described with reference to embodiments which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Primer Sequence 5'-NTR-1-21

<400> SEQUENCE: 1

```
gccagccccc tgatgggggc gacactccac                                    30
```

<210> SEQ ID NO 2
<211> LENGTH: 48
<212> TYPE: DNA
<213> ORGANISM: Artificial Sequence
<220> FEATURE:
<223> OTHER INFORMATION: Primer Sequence T7-SNTR-341-317

<400> SEQUENCE: 2

```
gaaattaata cgactcacta tagggggtgc acggtctacg agacctcc                48
```

What is claimed is:

1. A compound of Formula I or a pharmaceutically acceptable salt thereof, wherein Formula I is

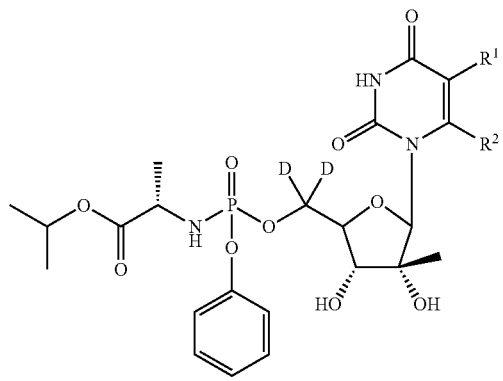

Formula I wherein $R^1$ and $R^2$ are each hydrogen or D; and each position represented as D has deuterium enrichment of at least 50%.

2. A compound or salt of claim 1 of the formula

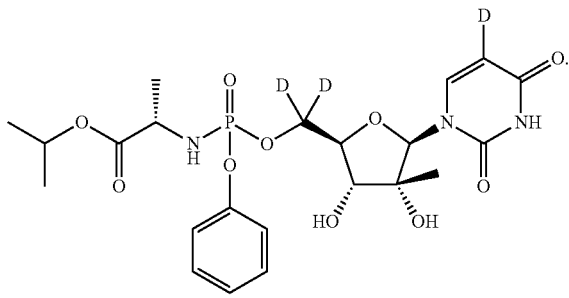 [SMILES: [2H]c1cn([C@@H]2O[C@H](C([2H])([2H])OP(=O)(N[C@@H](C)C(=O)OC(C)C)Oc3ccccc3)[C@@H](O)[C@@]2(C)O)c(=O)[nH]c1=O]

3. A compound or salt of claim 2 of the formula

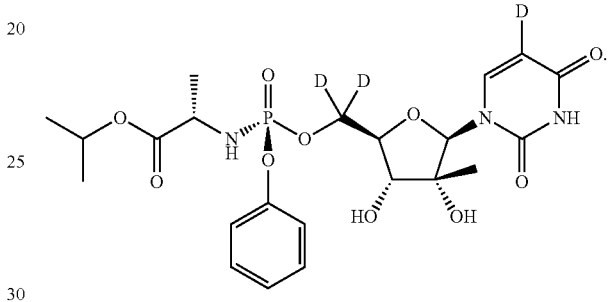

4. A compound or salt of claim 2 of the formula

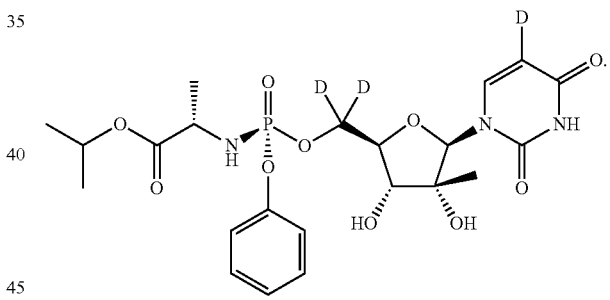

5. A compound or salt of claim 2, wherein each position represented as D has deuterium enrichment of at least 90%.

6. A compound of salt of claim 2, wherein each position represented as D has deuterium enrichment of at least 95%.

7. A 50/50 mixture of stereoisomers of the compound of claim 2, wherein the mixture is

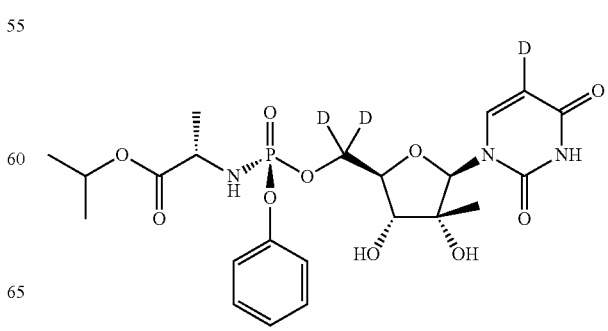

-continued
and

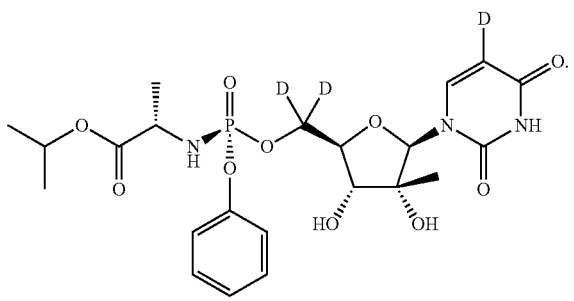 [SMILES: [2H]c1cn([C@@H]2O[C@H](C([2H])([2H])O[P@](=O)(N[C@@H](C)C(=O)OC(C)C)Oc3ccccc3)[C@@H](O)[C@@]2(C)O)c(=O)[nH]c1=O]

8. A pharmaceutical composition comprising an active agent, wherein the active agent is a compound or salt of claim 2, and also comprising a pharmaceutically acceptable carrier.

9. The pharmaceutical composition of claim 8, further comprising at least one additional active agent(s).

10. The pharmaceutical composition of claim 9, wherein the at least one additional active agent(s) are an HCV NS3 protease inhibitor, an HCV NS5A inhibitor, an HCV NS5B inhibitor, or a combination of the foregoing.

11. The pharmaceutical composition of claim 9, wherein the at least one additional active agents is an NS5A inhibitor and at least one of sovaprevir.

12. A method of treating an HCV infection in a patient in need thereof, comprising administering a therapeutically effective amount of a compound or salt of claim 2 to the patient in need thereof.

13. A method of treating an HCV infection in a patient in need thereof, comprising administering a therapeutically effective amount of a pharmaceutical composition of claim 8 to the patient in need thereof.

* * * * *